US007586008B2

(12) United States Patent
Tao et al.

(10) Patent No.: US 7,586,008 B2
(45) Date of Patent: Sep. 8, 2009

(54) PROPOFOL ANALOGS, PROCESS FOR THEIR PREPARATION, AND METHODS OF USE

(75) Inventors: Chunlin Tao, Los Angeles, CA (US);
Cheng Zhi Yu, San Diego, CA (US);
Neil P. Desai, Los Angeles, CA (US);
Vuong Trieu, Calabasas, CA (US)

(73) Assignee: Abraxis Bioscience, Inc., Los Angeles, CA (US)

( * ) Notice: Subject to any disclaimer, the term of this patent is extended or adjusted under 35 U.S.C. 154(b) by 0 days.

(21) Appl. No.: 12/170,314

(22) Filed: Jul. 9, 2008

(65) Prior Publication Data

US 2008/0275100 A1 Nov. 6, 2008

Related U.S. Application Data

(63) Continuation of application No. 10/584,017, filed as application No. PCT/US2004/043979 on Dec. 23, 2004, now abandoned.

(60) Provisional application No. 60/531,954, filed on Dec. 23, 2003.

(51) Int. Cl.
| | |
|---|---|
| C07C 49/00 | (2006.01) |
| C07C 325/00 | (2006.01) |
| C07F 9/02 | (2006.01) |
| A61K 31/12 | (2006.01) |
| A61K 31/125 | (2006.01) |

(52) U.S. Cl. ............................ 568/325; 568/20; 568/25; 568/333; 568/336; 558/177; 514/438; 514/675; 514/687; 514/690

(58) Field of Classification Search ........................ None
See application file for complete search history.

(56) References Cited

U.S. PATENT DOCUMENTS

| | | | |
|---|---|---|---|
| 2,841,624 | A | 7/1958 | Norton et al. |
| 3,215,530 | A | 11/1965 | Riebel et al. |
| 3,335,164 | A | 8/1967 | Scherer et al. |
| 4,001,277 | A | 1/1977 | Karger et al. |
| 4,009,210 | A | 2/1977 | Cahoy |
| 4,039,630 | A | 8/1977 | Kanagawa et al. |
| 5,308,874 | A | 5/1994 | Sanchez et al. |
| 5,461,080 | A | 10/1995 | Sanchez et al. |
| 5,916,596 | A | 6/1999 | Desai et al. |
| 6,506,405 | B1 | 1/2003 | Desai et al. |
| 6,537,579 | B1 | 3/2003 | Desai et al. |

FOREIGN PATENT DOCUMENTS

| | | |
|---|---|---|
| DE | 11 19 293 B | 12/1961 |
| EP | 0 334 119 A1 | 9/1989 |
| EP | 0 559 079 A1 | 9/1993 |
| EP | 0 625 507 A2 | 11/1994 |
| JP | 01 180878 A | 7/1989 |
| JP | 04 175768 A | 6/1992 |
| JP | 10 039525 A | 2/1998 |
| JP | 2001-288135 A | 10/2001 |
| WO | WO 93/20078 A1 | 10/1993 |
| WO | WO 01/26656 A2 | 4/2001 |
| WO | WO 03/009839 A1 | 2/2003 |

OTHER PUBLICATIONS

Auvin et al., *Bioorganic & Med. Chem. Letters*, 13(2), 209-212 (from Chemical Abstracts Service, accession No. 2002:943608) (2003).
Baik et al., *J. Organic Chem.*, 65 (1), 108-115 (from Chemical Abstracts Service, accession No. 1999:799959) (2000).
Coleman et al., *J. Macromolecular Science, Physics*, B38(4), 403-417 (from Chemical Abstracts Service, accession No. 1999:412556) (1999).
Finnegan et al., *J. Pharmaceutical Sciences*, 62(3), 483-485, (from Chemical Abstracts Service, accession No. 1973:413423) (1973).
Laali, Khosrow, *J. Org. Chem.*, 50(19), 3638-3640 (from Chemical Abstracts Service, accession No. 1985: 522669) (1985).
Rolls et al., *Polymer*, 31(1), 165-174 (from Chemical Abstracts Service, accession No. 1990:180411) (1990).
Rolls et al., *J. Chromatography*, 504(1), 97-112, (abstract from Chemical Abstracts Service, accession No. 1990:417250) (1990).
Roth et al., *J. Med. Chem.*, 31(1), 122-129 (from Chemical Abstracts Service, accession No. 1988:56055) (1988).
Stroh et al., *Angew. Chem.*, 69, 699-706 (from Chemical Abstracts Service, accession No. 1958:34968) (1957).
Volod'Kin et al., *Izvestiya Akademii Nauk SSSR*, 1, 174-176 (from Chemical Abstracts Service, accession No. 1996: 67458) (1966).
Search Report—EP 04 81 5966 (Sep. 6, 2007).
Bai et al. *J. Neuroscience*, 19(24), 10635-10646 (Dec. 15, 1999).
Barnard et al., *Pharm. Rev.*, 50(2), 291-313 (1998).
Bennett et al., *Bioorganic & Med. Chem. Lett.*, 13, 1971-1975 (2003).
Eghbali et al., *European. J. Pharm.*, 468, 75-82 (2003).
Hales et al., *Br. J. Pharmacol.*, 104, 619-628 (1991).
James et al., *J. Med. Chem.*, 23, 1350-1357 (1980).
Jevtovic-Todorovic et al., *Brain Res.*, 913, 185-189 (2001).
Jones et al., *J. of Pharmacology and Exp. Therapeutics*, 274(2), 962-968 (1995).
Kelly et al., *J. Neurosurg.*, 90, 1042-1052 (Jun. 1999).
Krasowski et al., *J. of Pharmacology and Exp. Therapeutics*, 297(1) 338-351 (2001).
Krasowski et al., *J. Med. Chem.*, 45, 3210-3221 (2002).
Lam et al., *Brain Res.*, 784, 179-187 (1998).
Langley et al., *Drugs*, 35, 334-372 (1988).
Orser et al., *J. Neuroscience*, 14(12), 7747-7760 (Dec. 1994).
Patel et al., *Br. J. Pharmacology*, 139, 1005-1013 (2003).
Peng et al., *Chinese Med. J.*, 116(5), 731-735 (2003).
Rees et al., *Ann. Rep. Med. Chem.*, 31, 41-50 (1996).
Robb et al., *Br. Dent. J.*, 194 (9), 469-471 (May 2003).
Sagara et al., *J. Neurochem.*, 2524-2530 (1999).
Sanna et al., *Mol. Pharmacology*, 47, 213-217 (1995).
Sieghart, *Pharmacological Rev.*, 47(2), 181-234 (1995).
Sneyd, *J. Royal Soc. Med.*, 85, 288-291 (May 1992).
Trapani et al., *J. Med. Chem.*, 41, 1846-1854 (1998).
Trapani et al., *Curr. Med. Chem.*, 7, 249-271 (2000).
Tsuchiya et al., *Am. J. Respir. Crit. Care Med.*, 165, 54-60 (2002).
Williams et al., *J. Neuroscience*, 22(17), 7417-7424 (Sep. 1, 2002).
Xia et al., *Cardiovascular Res.*, 59, 113-121 (2003).

*Primary Examiner*—Sikarl A Witherspoon
(74) *Attorney, Agent, or Firm*—Leydig, Voit & Mayer, Ltd.

(57) ABSTRACT

The invention provides para substituted dialkylphenol derivatives of propofol. The invention further provides pharmaceutical compositions comprising such analogs, methods for preparing such analogs, and methods of using such analogs to induce general anesthesia, sedation, and/or hypnotic or sleep effects in a patient.

28 Claims, No Drawings

PROPOFOL ANALOGS, PROCESS FOR THEIR PREPARATION, AND METHODS OF USE

CROSS-REFERENCE TO RELATED PATENT APPLICATIONS

This patent application is a continuation of copending U.S. patent application Ser. No. 10/584,017, filed as the U.S. national phase entry on Jun. 22, 2006 (with a Section 371(c) date of Jan. 23, 2007) of PCT Application No. PCT/US04/43979, filed on Dec. 23, 2004, all of which are incorporated by reference in their entireties herein. This patent application claims the benefit of U.S. Provisional Patent Application No. 60/531,954, filed on Dec. 23, 2003, which is incorporated by reference in its entirety herein.

FIELD OF THE INVENTION

The present invention relates to derivatives of propofol. More particularly, the invention relates to para-substituted dialkylphenol propofol compounds, processes for their preparation, and pharmaceutical compositions containing them.

BACKGROUND OF THE INVENTION

Propofol (2,6-diisopropylphenol, formula I), is a short-acting hypnotic agent, effective for induction and maintenance of anesthesia (see, e.g., Rees et al., *Annu. Rep. Med. Chem.*, 31, 41-50 (1996), and Trapani et al., *Curr. Med. Chem.*, 7, 249 (2000)). Propofol also is used for intravenous (iv) sedation by target-controlled infusions (see, e.g., Leitch, *Br. Dent. J.*, 194, 443 (2003)).

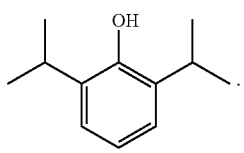

(I)

Induction of anesthesia with propofol is rapid, and maintenance can be achieved by continuous infusion or by intermittent bolus doses. Propofol is becoming the anesthetic of choice for ambulatory surgery in outpatients. Its greatest advantage is rapid recovery, even after long periods of anesthesia. A particularly low incidence of postoperative nausea and vomiting also has been observed. Disadvantages of propofol include a relatively high incidence of apnea, blood pressure reductions, and pain upon injection.

A large body of experimental evidence accumulated in the past decade demonstrates that the inhibitory central GABAergic neurotransmission represents an important target in mediating some of the pharmacological actions of propofol. GABA is the major inhibitory neurotransmitter in the vertebrate central nervous system (CNS), whose action is produced by its selective interaction with at least two classes of GABA receptors, namely $GABA_A$ and $GABA_B$ receptors. While $GABA_B$ receptors are members of the G-protein-linked receptor superfamily and are coupled with $K^+$ and $Ca^{+2}$ channels, $GABA_A$ receptors are an allosteric inhibitory neurotransmitter-gated ion channel coupled to an integral chloride channel (see, e.g., Sieghart, *Pharmacol. Rev.*, 47, 181 (1995)). $GABA_A$ receptors are composed of a number of phylogenetically related subunits ($\alpha$1-6, $\beta$1-4, $\gamma$1-3, $\delta$, $\epsilon$, $\rho$1-3), that coassemble to form a pentameric structure which contains a central $Cl^-$ channel. $GABA_A$ receptors express a complex pharmacology. It has been reported that a number of distinct classed of drugs (e.g., benzodiazepines and benzodiazepine-like compounds, beta-carbolines, steroids, barbiturates, alcohols, picrotoxin, and tert-butylbicyclophosphorothionate (TBOB) exert their effects by interacting with specific modulatory sites on this receptor (see, e.g., Barnard et al., *Pharmacol Rev.*, 50, 291 (1998)). The effects of propofol on $GABA_A$ channel conductance in rat-cultured hippocampal neurons also have been reported (see, e.g., Eghbali et al., *Eur. J. Pharmacol.*, 468(2), 75-82 (2003)). The extracellular domain of the $GABA_A$ receptor contains two GABA binding sites that, when occupied, induce channel opening and subsequent desensitization. The receptor also has binding sites for allosteric modulators, including some general anesthetics.

It has been observed that the action of general anesthetics may be mediated by a specific subunit of the $GABA_A$ receptor (see, e.g., Sanna et al., *Mol. Pharmacol.*, 47, 213 (1995)). Indeed, propofol has been shown to produce a strong $Cl^-$ current activation at $\beta$1 homomeric receptors as well as at $\alpha1\beta1$, $\alpha1\beta1\gamma2$, and $\beta1\gamma2$ receptors. Propofol has been shown in electrophysiological assays to allosterically enhance the action of GABA at the $GABA_A$ receptor (see, e.g., Hales et al., *Br. J. Pharmcol.*, 104, 619 (1991)), and also to prolong inhibitory postsynaptic currents mediated by $GABA_A$ receptors (see, e.g., Orser et al., *J. Neurosci.*, 14, 7747 (1994)). Propofol can also open the $GABA_A$ receptor ion channel in the absence of GABA, although this usually occurs at higher concentrations of propofol than necessary to potentiate submaximal receptor response of GABA (see, e.g., Jones et al., *J. Pharmacol. Exp. Ther.*, 274, 962 (1995)). It also has been observed that propofol and analogs thereof produced loss of righting reflex in tadpoles in the action at the $GABA_A$ $\alpha1\beta2\gamma2s$ receptor (see, e.g., Krasowski et al, *J. Pharmacol. Exp. Ther.*, 297, 338 (2001)).

Recently, Patel et al., *Br. J. of Pharm.*, 139, 1005 (2003) reported that propofol activation of the endocannabinoid system, possibly via inhibition of anandamide catabolism, contributes to the sedative properties of propofol, and that fatty acid amide hydrolase could be a novel target for anesthetic development.

Propofol does not bind at the GABA binding sites. It may bind in a crevice near the extracellular ends of the $\beta$ subunit M2 and M3 membrane-spanning segments (see, e.g., Williams et al., *J. Neurosci.*, 22, 7417 (2002)). The effects of propofol on channel kinetics suggest that it stabilizes as a double ligand, pre-open, nonconducting state (see, e.g., Bai et al., *J. Neurosci.*, 19, 10635 (1999)). At low concentration (0.5 $\mu$M), propofol potentiates current induced by submaximal GABA concentrations but does not directly activate $GABA_A$ receptors. At 20-fold higher concentrations, propofol directly activates receptors, causing channel opening in the absence of GABA (see, e.g., Lam and Reynolds, *Brain Res.*, 784, 178 (1998)).

Propofol has been used in the treatment of pathologies relating to the presence of free oxygen radicals (see, e.g., U.S. Pat. Nos. 5,308,874 and 5,461,080). Propofol has been shown to repair neural damage caused by free oxygen radicals in vitro (see, e.g., Sagara et al., *J. Neurochem.*, 73, 2524 (1999) and Jevtovic-Todorovic et al., *Brain Res.*, 913, 185 (2001)) and has been used in vivo to treat head injury (see, e.g., Kelly et al., *J. of Neurosurgery*, 90, 1042 (1999)).

There is evidence suggesting that propofol can protect endothelial cells against oxidative stress by inhibiting eNOS transcription and protein expression (see, e.g., Peng et al., *Chin. Med. J.* (Engl)., 116(5), 731-5 (2003)). Moreover, propofol enhances ischemic tolerance of middle-aged hearts, primarily by inhibiting lipid peroxidation (see, e.g., Xia et al., *Cardiovasc. Res.*, 59, 113 (2003)).

The search for novel high-affinity ligands for the $GABA_A$ receptor has led to the synthesis of numerous propofol analogs, and to the determination of a structure-activity relationship of propofol binding affinity to $GABA_A$ (reviewed by, e.g., Trapani et al., *Curr. Med. Chem.*, 7, 249 (2000)). The preparation of propofol analogs has been disclosed in, for example, Trapani et al., *J. Med. Chem.*, 41, 1846 (1998).

It is possible to modify the molecular structure of propofol in order to optimize all its various activities (e.g., anesthetic, sedative, and anticonvulsant activities) or to yield drugs with more selective actions. Introduction of halogen or benzoyl substituents in the para position of the phenyl group of propofol yielded a series of molecules that inhibit the binding of t-[$^{35}$S]butylbicylcophosphorothionate to $GABA_A$ receptors and potentiate GABA-evoked currents at these receptors with an efficacy similar to or higher than that of propofol (see, e.g., Trapani et al., supra).

The only recognized method for delivery of alkylphenols is by intravenous injection in a lipid-based emulsion. After iv administration, propofol is rapidly distributed from the blood into highly perfused areas such as heart, lung, and liver, and to tissues because of its high solubility in lipids. This high solubility enables propofol to cross the blood-brain barrier easily.

From a clinical viewpoint, several adverse effects have been found in patients undergoing treatment with propofol oil-emulsion. These include pain on injection, apnea, reduction in blood pressure, bradycardia, and excitatory events including convulsions (see, e.g., Langley et al., *Drugs*, 33, 334 (1988), Rees et al., *Annu. Rep. Med. Chem.*, 31, 41 (1996), and Sneyd et al., *J. R. Soc. Med.*, 85, 288 (1992)).

Recently, Bennett et al., *Bioorg. Med. Chem. Lett.*, 13, 1971 (2003) disclosed the general anesthetic activity of a series of amino-2,6-dimethoxyphenyl ester derivatives. The new chemicals exhibit improved anesthetic activity in mice relative to propofol.

Therefore, there is a need for propofol analogs and methods for using propofol analogs to induce general anesthesia, a hypnotic effect, or sleep inducement in a subject. The invention provides such analogs and methods of use. Specifically, the invention provides propofol derivatives that can be used for anesthetic effect generally, and in small doses for hypnotic effect, sedation, or sleep inducement. The new compounds are substantially more active in inducing an anesthetic effect than propofol itself. The result of this increased activity means that the compounds can be used in larger doses for general anesthesia, but in smaller doses to induce a hypnotic effect, sedation, and sleep effect, thereby resulting in a reduction in propofol-related side effects (e.g., cardiovascular side effects). These and other advantages of the invention, as well as additional inventive features, will be apparent from the description of the invention provided herein.

BRIEF SUMMARY OF THE INVENTION

In accordance with one aspect of the invention, there are provided propofol derivatives, specifically para-substituted dialkylphenol propofol derivatives. In another aspect of the invention, there is provided a method of preparing the above-described dialkylphenol derivatives of propofol. In various embodiments, the invention provides a pharmaceutical composition comprising a propofol derivative as described above and a pharmaceutically acceptable carrier. In still other aspects of the invention, there is provided a method of using propofol derivatives to induce general anesthesia, sedation, and/or hypnotic or sleep effects.

DETAILED DESCRIPTION OF THE INVENTION

The para-substituted dialkylphylphenol propofol derivatives in accordance with the present invention are represented by Formula (II), as follows:

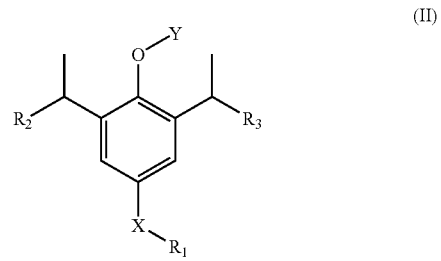

(II)

wherein,
$R_1$ is hydrogen, $C_1$-$C_6$ alkyl, or $C_4$-$C_{20}$ aryl, and
$R_2$ and $R_3$ are hydrogen, or $C_1$-$C_6$ alkyl.
X is C=O, C=S, C=C, $CR_4R_5$, $C(OR_6)R_7$, or C=N—$OR_8$.
Y is hydrogen, $COR_4$, $COOR_4$, $CONR_4R_5$, $COSR_4$, phosphate.

wherein
$R_4$, $R_5$, $R_6$, $R_7$ and $R_8$ are hydrogen, or $C_1$-$C_6$ alkyl.

An illustrative embodiment of the present invention is a compound of formula II, wherein $R_1$ is hydrogen, $C_1$-$C_6$ alkyl, or $C_4$-$C_{20}$ aryl; $R_2$ and $R_3$ are hydrogen or $C_1$-$C_6$ alkyl; X is C=O and Y is H.

The following definitions refer to the various terms used above and throughout the disclosure.

The term "$C_1$-$C_6$ alkyl" refers to straight or branched, substituted or unsubstituted, aliphatic groups of 1-6 carbon atoms including, for example, methyl, ethyl, propyl, isopropyl, cyclopropyl, n-butyl, isobutyl, sec-butyl, cyclobutyl, tert-butyl, pentyl, hexyl, and cyclohexyl.

The term "$C_4$-$C_{20}$ aryl" refers to an aromatic or heteroaromatic ring including, by way of example, phenyl, naphthyl, furanyl, and thionyl. The aryl ring can be unsubstituted or it can be substituted. Substituents halo (e.g. fluoro, chloro, bromo and iodo) $C_1$-$C_6$ alkyl which can be substituted, for example, by halogen, $C_1$-$C_6$ alkoxy —$NO_2$, —CN, anhydride, phenyl amino, carboxyl and alkyl substituted amino. The aryl ring can be substituted with any of one, two, three, four, five or more substituents, depending on the size of the ring. Examples of suitable $C_4$-$C_{20}$ aryl groups include, for example, 4-chlorophenyl, 3-chlorophenyl, 2-chlorophenyl, 4-trifluoromethylphenyl, 3-trifluoromethylphenyl, 2-trifluoromethylphenyl, 4-methoxyphenyl, 3-methoxyphenyl, 2-methoxyphenyl, 4-nitrophenyl, 3-nitrophenyl, 2-nitrophenyl, 4-cyanophenyl, 3-cyanophenyl, 2-methylphenyl, 4-methylphenyl, 3-chloromethylphenyl, 4-bromomethylphenyl, 2-ethylphenyl, 3-propylphenyl, 2-iodophenyl, 4-iodophenyl, 4-trifluoromethoxyphenyl, 4-butoxyphenyl, 4-biphenyl, 1-naphthalenyl, 2-naphthalenyl, 2-furanyl, 5-nitro-2-furanyl, 2-thiophenyl, 3,4-methylenedioxyphenyl, 2,4-dimethoxyphenyl, 2,6-dimethoxyphenyl, 3,4-dimethyoxyphenyl, 3,5-dimethoxyphenyl, 2,3-difluorophenyl, 2,4-difluorophenyl, 2,5-difluorophenyl, 2,6-difluorophenyl, 3,4-difluorophenyl, 3,5-difluorophenyl, 2,4-dichlorophenyl, 2,6-dichlorophenyl, 3,5-dichlorophenyl, 2,5-bis(trifluoromethyl)phenyl, 3,5-bis(trifluoromethyl)phenyl, 4-chloro-3-nitrophenyl, 5-bromo-2-methoxyphenyl, 2-fluoro-3-trifluoromethylphenyl, 2-fluoro-5-trifluoromethylphenyl, 2-fluoro-6-trifluoromethylphenyl, 3-fluoro-4-trifluoromethylphenyl, 3-fluoro-5-trifluoromethylphenyl, 2,3,4-trifluorophenyl, 2,3,6-trifluorophenyl, 2,4,5-trifluorophenyl, 2,4,6-trichlorophenyl, 2,4-dichloro-5-fluorophenyl, 3,4,5-trimethoxyphenyl, 2,4,5-trifluoro-3-methoxyphenyl, 2,3,4,5-tetrafluorophenyl, pentafluorophenyl, 4,5-diphenyl-imidazol-2-yl, and the like.

The term "$C_1$-$C_6$ alkoxy" includes the straight or branched aliphatic ether functionalities of 1-6 carbon atoms such as, for example, methoxy, ethoxy, propoxy, isopropoxy, n-butoxy, isobutoxy, sec-butoxy, tert-butoxy, pentoxy, hexoxy, cyclohexoxy, and phenoxy.

The compounds of Formula II are useful to induce general anesthesia, hypnosis, sedation and sleep in a subject, particularly in mammals, and most preferably in humans. In preferred embodiments of the invention, in the compounds represented by Formula II, $R_1$ is a substituted phenyl, and $R_2$ and $R_3$ are $C_1$-$C_4$ alkyl. Most preferably, $R_3$ is a 4-substituted phenyl, and $R_2$ and $R_3$ are methyl and ethyl, respectively. Preferred 4-substituted phenyl groups are 4-fluorophenyl, 4-chlorophenyl, 4-bromophenyl, 4-trifluoromethylphenyl, 4-methoxyphenyl, 4-nitrophenyl, 4-cyanophenyl, 4-methylphenyl, 4-iodophenyl, 4-trifluoromethoxyphenyl, 4-bromomethylphenyl, 4-dimethylaminophenyl, and 4-biphenyl.

Preferred embodiments falling within the scope of this invention are as follows:

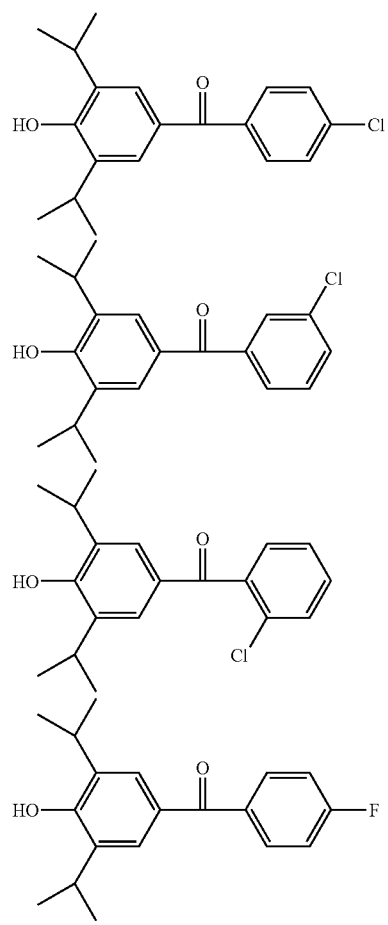

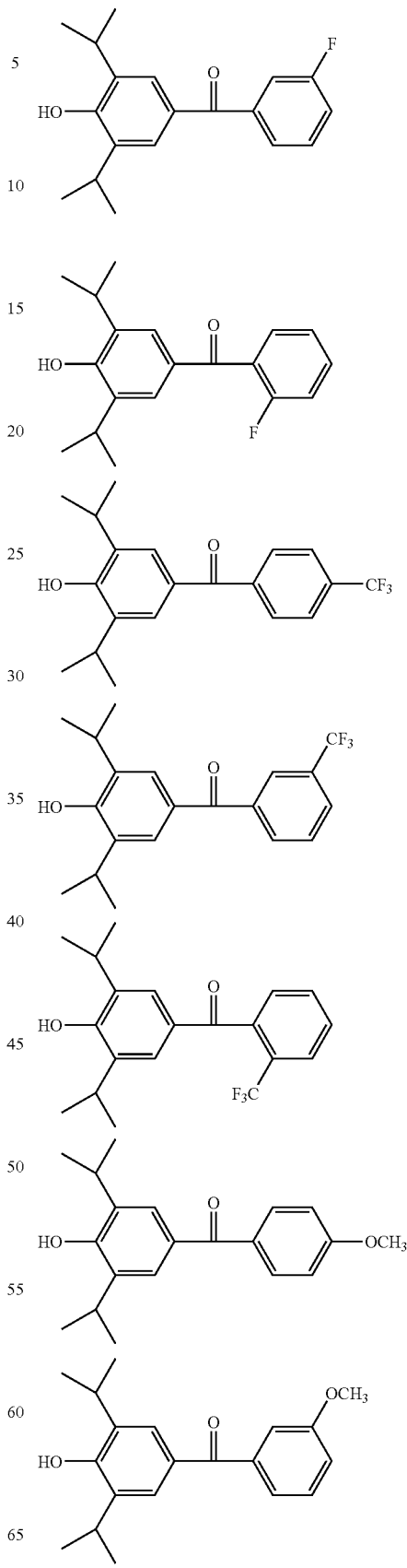

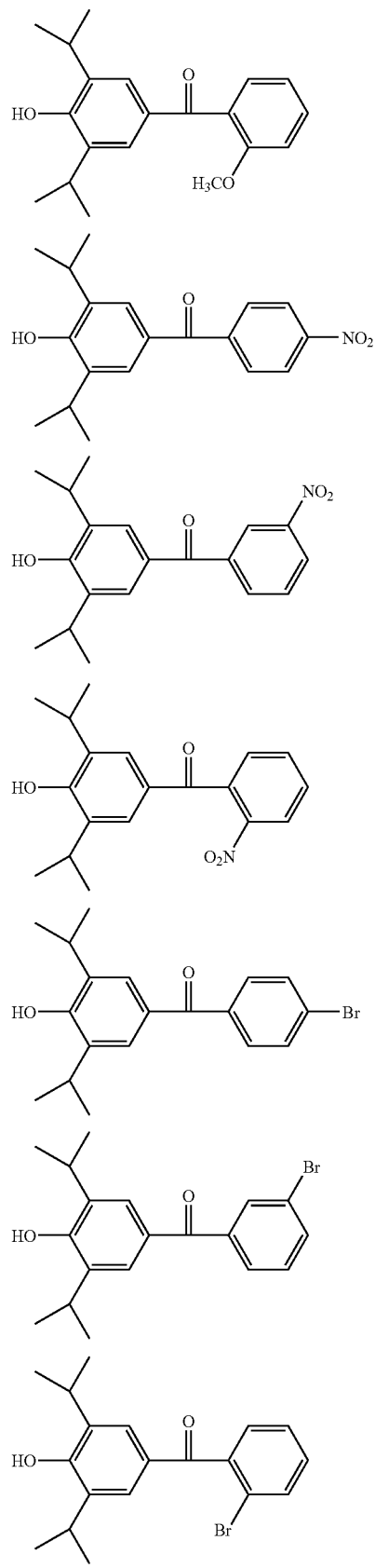
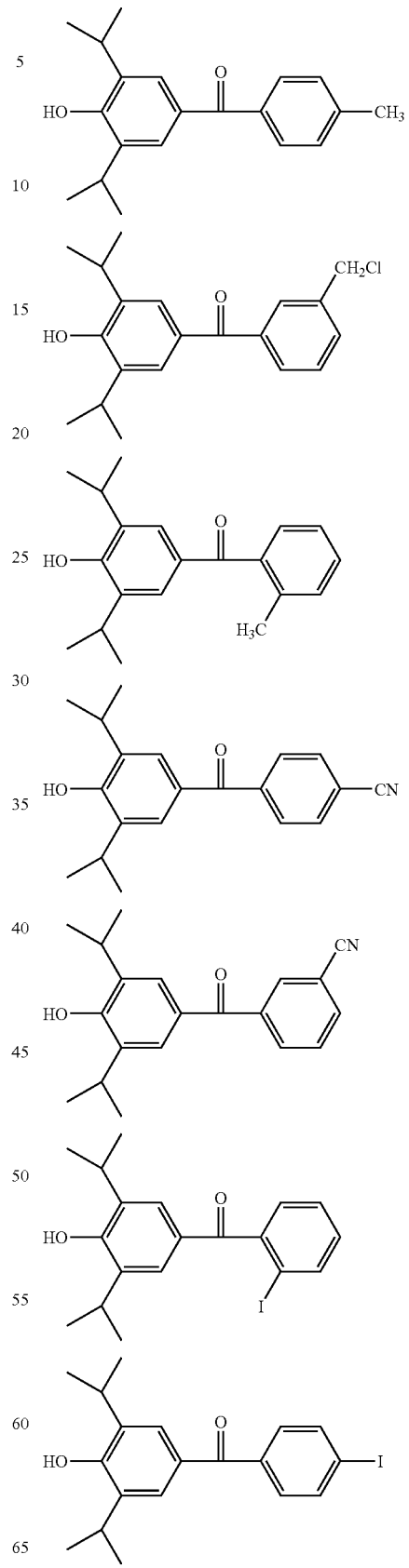

-continued
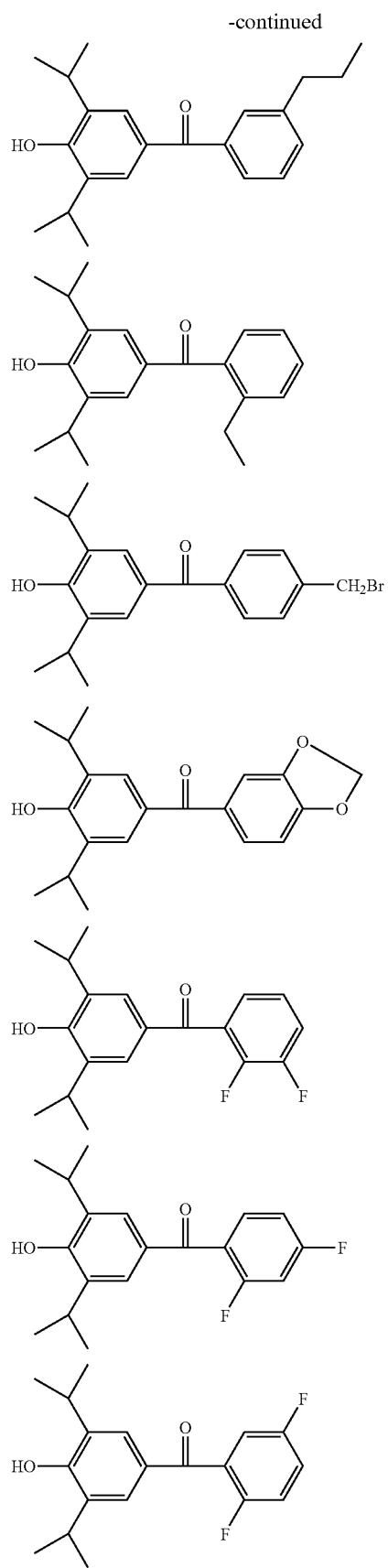
-continued
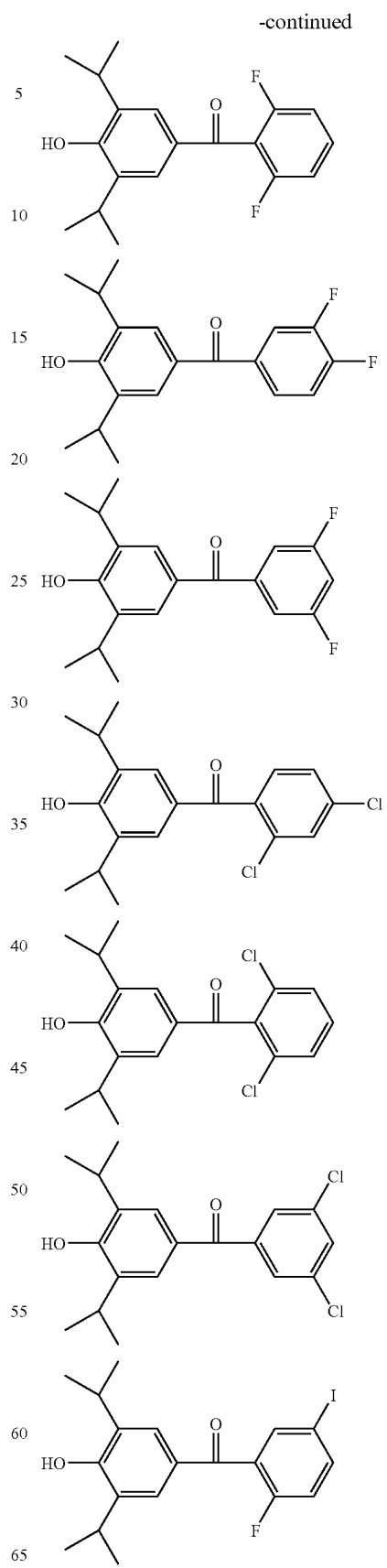

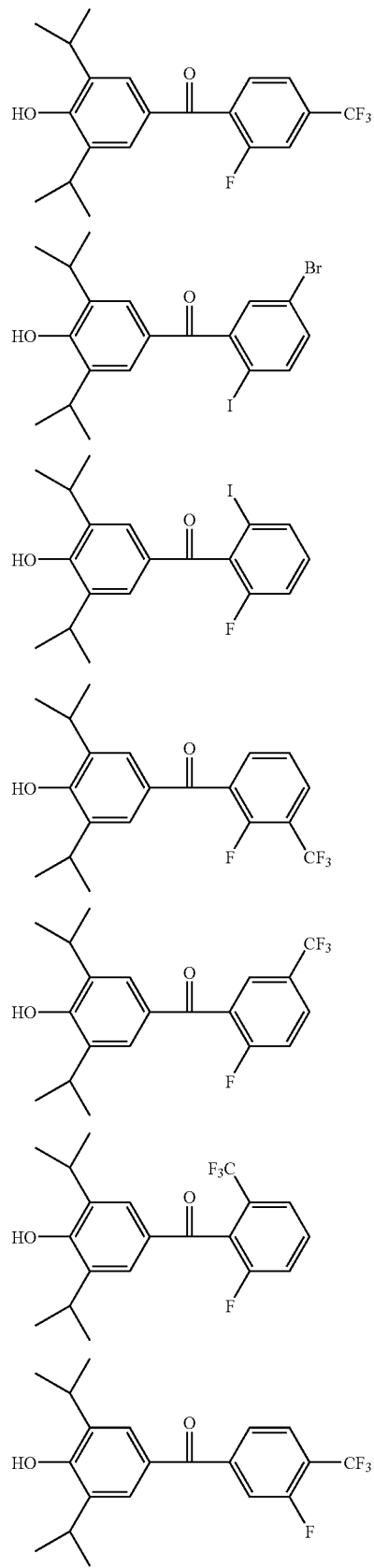
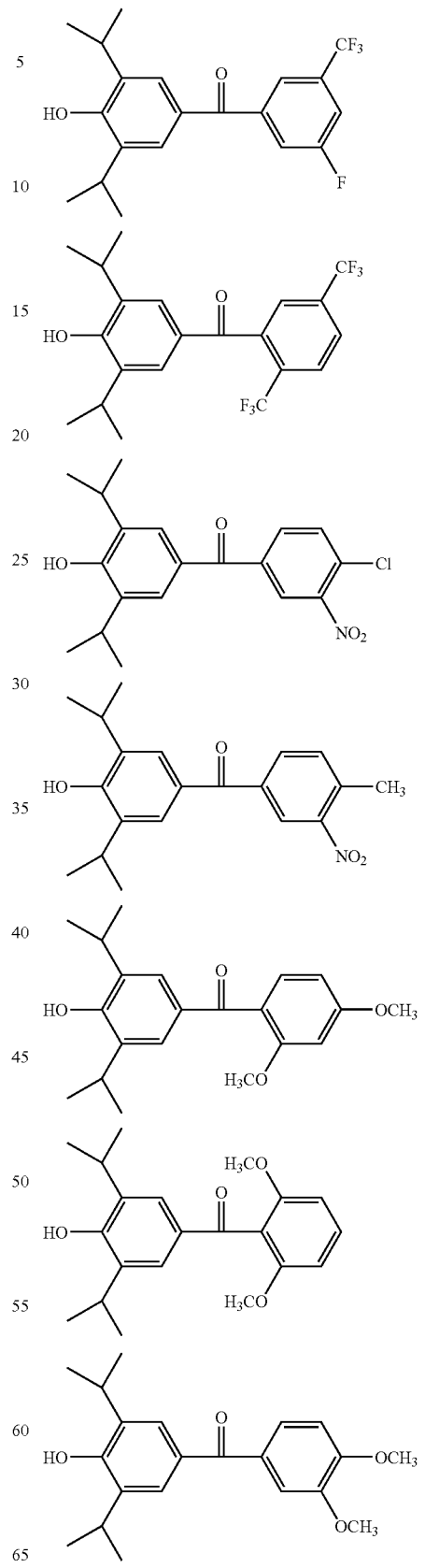

-continued
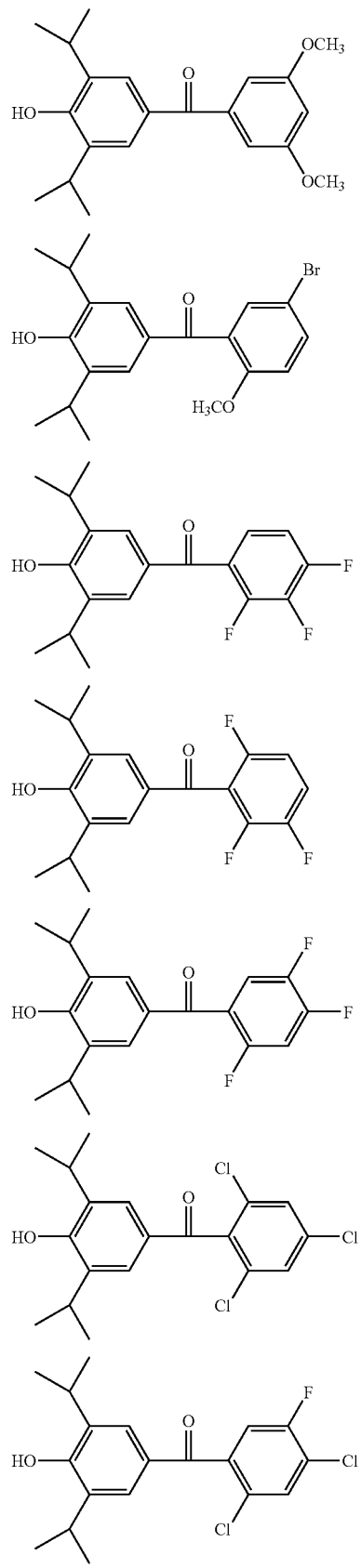
-continued
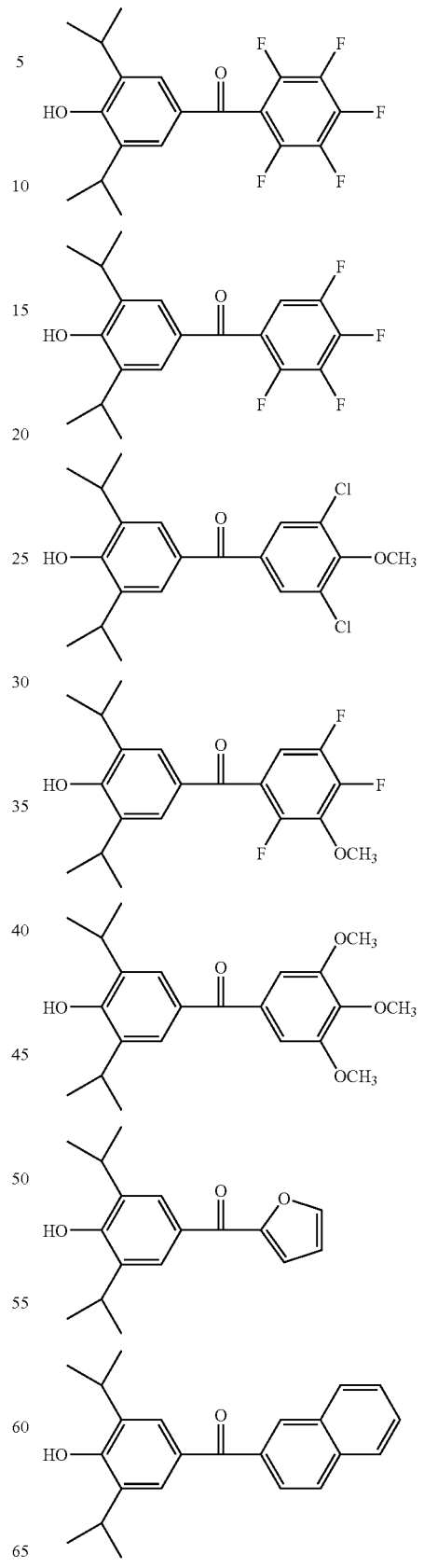

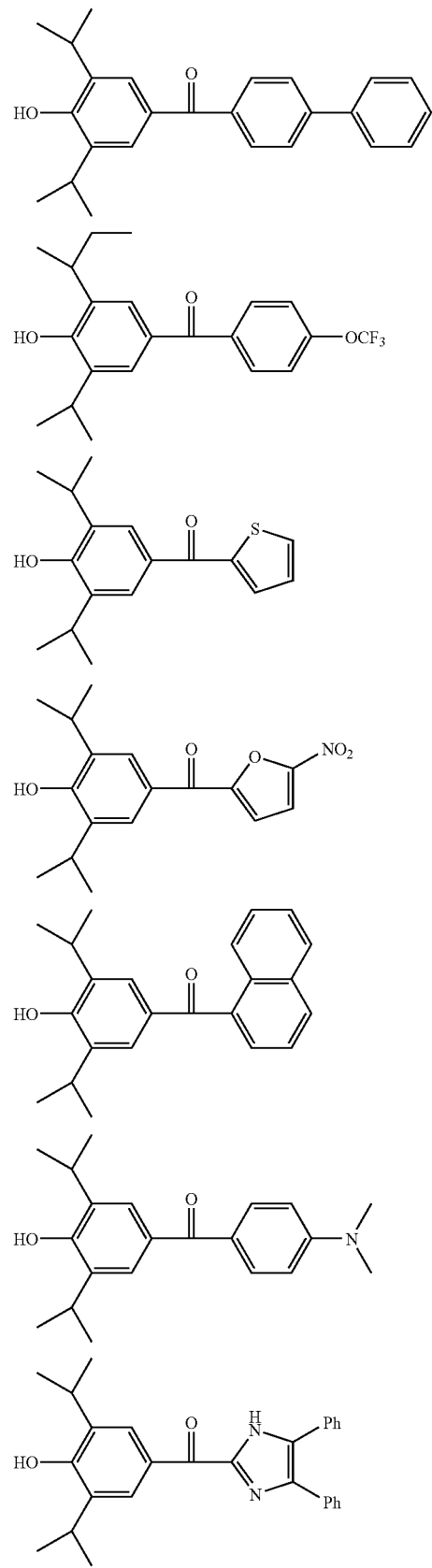
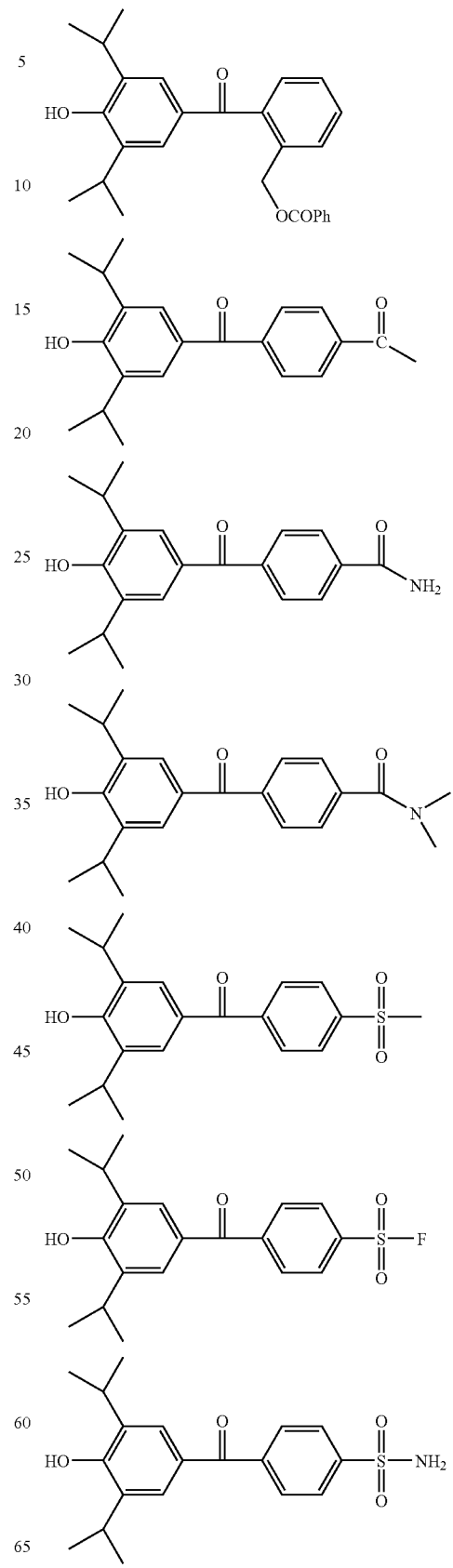

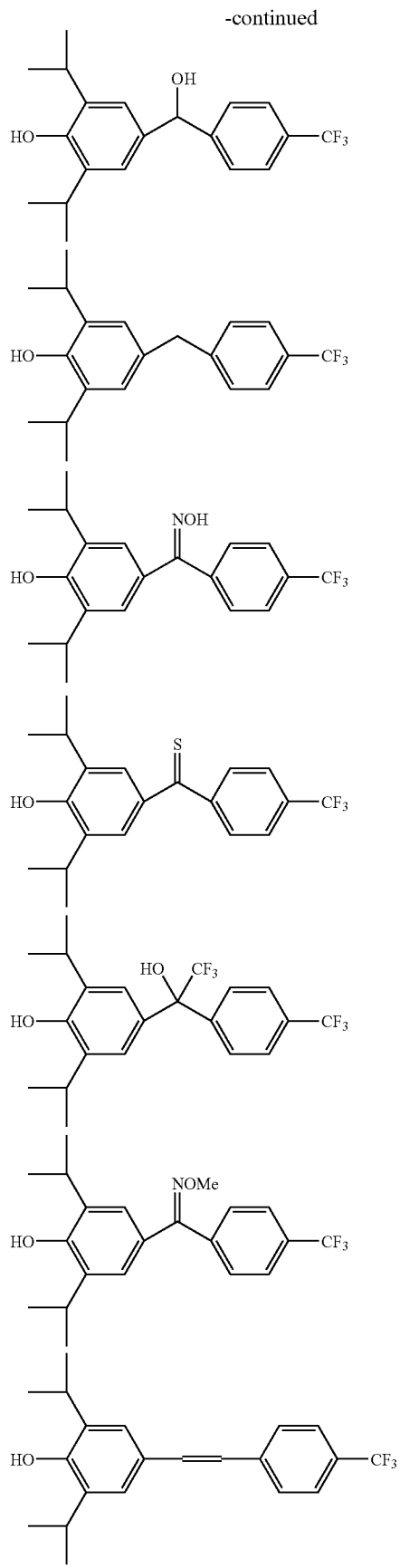

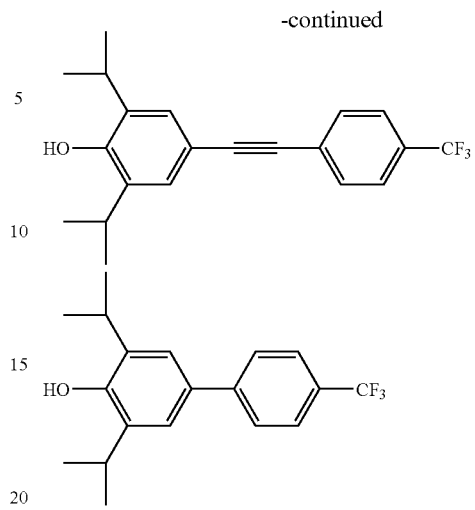

The preparation of formula II preferably is carried out as illustrated in Scheme 1:

SCHEME 1

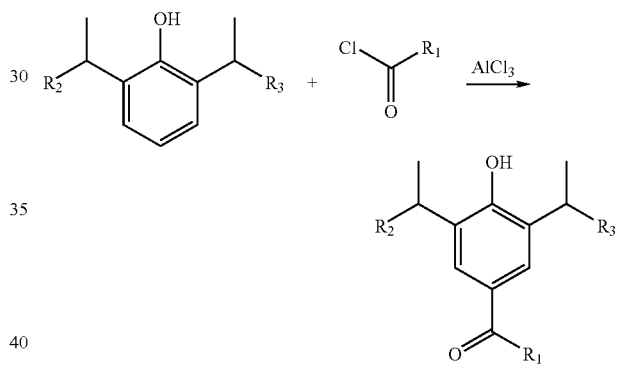

The compounds of present invention are prepared as illustrated in Scheme 1. The mixture of 2,6-dialkyl phenol is treated with acyl chloride in the presence of Lewis acid, such as aluminum chloride, titanium tetrachloride, or zinc chloride for 1-24 hours. The reaction can be carried out in either toluene, dichloromethane, or other anhydrous solvent. After reaction, the mixture is quenched with ice water and extracted with organic solvent, such as ether, ethyl acetate, dichloromethane, chloroform, and the like. After removal of organic solvent, the residue can be purified with general flash column chromatography to afford the desired product, and can be accompanied by an ester of the desired product, which can be hydrolyzed by aqueous sodium hydroxide to produce the desired p-substituted 2,6-dialkylphenol.

The other starting materials employed in the manufacturing method of this invention are known in the art or can be made by methods described in the art. The preparative methods for various 2,6-dialkylphenol derivatives are disclosed in, for example, James and Glen, *J. Med. Chem.*, 23, 1350 (1980)).

Thus, in accordance with the invention, para-aryl phenol analogs can be prepared by the reaction of acyl halide with dialkyl phenol in the presence of a Lewis acid, such as aluminum chloride, titanium tetrachloride, zinc chloride, or the like. In general, any aryl acyl halide can be used for the preparation of the present invention. Since aryl acyl halides can be prepared from the corresponding aryl carboxylic acid according to the general procedure in the organic chemistry, many novel compounds can be prepared in accordance with the invention.

The compounds disclosed herein can be formulated into pharmaceutical compositions for administration to a patient, preferably a human patient. Any of a number of suitable pharmaceutical formulations can be utilized as a vehicle for the administration of the compounds of the invention. Preferably, the inventive compounds are formulated for general pharmaceutical use. Most preferably, the inventive compounds are formulated for use in anesthesia.

The composition can be administered to a patient by conventional administration methods for anesthetics, such as, for example, oral administration, nasal respiratory administration, bolus injection, intravenous administration by repeated doses or by continuous infusion, rectal administration, vaginal administration, sublingual administration, cutaneous administration, and slow release routes. Preferably, the pharmaceutical composition is administered by continuous infusion. In some embodiments, the pharmaceutical composition can be administered by two or more routes, such as by bolus injection followed by continuous intravenous administration.

Typically, the compound is mixed with a carrier, diluted by a carrier, or enclosed within a carrier which can be in the form of a capsule, sachet, paper, or other container. When the carrier serves as a diluent, it can be a solid, semi-solid, or liquid material which acts as a vehicle, excipient, or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments which contain, for example, up to 10% by weight of the active compound, soft and hard gelatin capsules, suppositories, sterile injectable solutions, and sterile packaged powders.

For oral administration, the active compound of the present invention can be incorporated into suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone, or gelatin.

Examples of suitable carriers, excipients, and diluents include, for example, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil. The formulations can additionally include lubricating agents, wetting agents, emulsifying and suspending agents, preserving agents, sweetening agents, or flavoring agents. The compositions can be formulated so as to provide rapid, sustained, or delayed release of the active ingredient after administration to the patient by employing procedures well known in the art.

Preferred compositions for administration by injection include those comprising a novel biologically active analogue as the active ingredient, in association with a surface-active agent (or wetting agent or surfactant), or in the form of an emulsion (e.g., as a water-in-oil or oil-in-water emulsion). Suitable surface-active agents include, in particular, nonionic agents, such as polyoxyethylenesorbitans (e.g., Tween™ 20, 40, 60, 80, or 85), and other sorbitans (e.g., Span™ 20, 40, 60, 80, or 85). Other ingredients can be added, for example, mannitol or other pharmaceutically acceptable vehicles, if necessary.

The invention also provides compositions comprising propofol derivatives and methods of using such compositions for the in vivo delivery of dialkylphenol derivatives in the form of nanoparticles, which are suitable for any aforesaid route of administration.

The invention also provides methods for the formation of nanoparticles of the inventive compounds by a solvent evaporation technique from an oil-in-water emulsion prepared under conditions of high shear forces (e.g., sonication, high pressure homogenization, or the like). The preparation of nanoparticles from biocompatible polymers (e.g., albumin) is disclosed in, for example, U.S. Pat. Nos. 5,916,596, 6,506,405, and 6,537,579.

Thus, in accordance with the present invention, propofol derivatives are dissolved in a water miscible organic solvent (e.g., a solvent having greater than about 10% solubility in water, such as, for example, ethanol) at a final concentration in the range of about 1-99% (v/v), more preferably in the range of about 5-25% (v/v) of the total organic phase. The water miscible organic solvent can be selected from solvents such as, for example, ethyl acetate, ethanol, tetrahydrofuran, dioxane, acetonitrile, acetone, dimethyl sulfoxide, dimethyl formamide, methyl pyrrolidinone, and the like. Alternatively, the mixture of water immiscible solvent with the water miscible solvent is prepared first, followed by dissolution of the pharmaceutically active agent in the mixture.

Next, a protein (e.g., human serum albumin) is added into the aqueous phase to act as a stabilizing agent for the formation of stable nanodroplets. Protein is added at a concentration in the range of about 0.05 to 25% (w/v), more preferably in the range of about 0.5-5% (w/v). Unlike conventional methods for nanoparticle formation, no surfactant (e.g. sodium lauryl sulfate, lecithin, Tween® 80, Pluronic® F-68, and the like) is added to the mixture. Optionally, a sufficient amount of the first organic solvent (e.g., chloroform) is dissolved in the aqueous phase to bring it close to the saturation concentration. A separate, measured amount of the organic phase (which now contains the pharmacologically active agent, the first organic solvent, and the second organic solvent) is added to the saturated aqueous phase, so that the phase fraction of the organic phase preferably is between about 0.5% and 15% (v/v), and more preferably is between 1% and 8% (v/v).

An emulsion is formed by homogenization under high pressure and high shear forces. Such homogenization is conveniently carried out in a high-pressure homogenizer, typically operated at pressures in the range of about 3,000 up to 30,000 psi. Preferably, such processes are carried out at pressures in the range of about 6,000 up to 25,000 psi. The resulting emulsion comprises very small nanodroplets of the nonaqueous solvent containing the dissolved pharmacologically active agent and very small nanodroplets of the protein-stabilizing agent. Acceptable methods of homogenization include processes imparting high shear and cavitation such as, for example, high-pressure homogenization, high shear mixers, sonication, high shear impellers, and the like.

The solvent is evaporated under reduced pressure to yield a colloidal system composed of protein-coated nanoparticles of pharmacologically active propofol analog and protein. Acceptable methods of evaporation include, for example, the use of rotary evaporators, falling film evaporators, spray driers, freeze driers, and the like. Thus, a colloidal dispersion system (pharmacologically active agent and protein) in the form of extremely small nanoparticles (e.g., particles in the range of about 10-200 nm diameter) can be sterile-filtered. The preferred size range of the particles is between about 50-170 nm (e.g., about 70 nm, about 100 µm, or about 150 nm), depending on the formulation and operational parameters.

Colloidal systems prepared in accordance with the present invention can be further converted into powder form by removal of the water, e.g., by lyophilization at a suitable temperature-time profile. The protein (e.g., human serum albumin) itself acts as a cryoprotectant, and the powder is easily reconstituted by addition of water, saline, or buffer, without the need to use conventional cryoprotectants such as mannitol, sucrose, glycine, and the like. While not required, it is of course understood that conventional cryoprotectants can be added to the pharmaceutical compositions if so desired.

The polymeric shell containing solid or liquid cores of pharmacologically active agent allows for the delivery of high doses of the pharmacologically active agent in relatively small volumes. This minimizes patient discomfort at receiving large volumes of fluid and minimizes hospital stay. In addition, the walls of the polymeric shell or coating are generally completely degradable in vivo by proteolytic enzymes (e.g., when the polymer is a protein), resulting in no side effects from the delivery system, as compared to current formulations.

A number of biocompatible materials can be employed in the formation of a polymeric shell. As used herein, the term "biocompatible" describes a substance that does not appreciably alter or affect in any adverse way, the biological system into which it is introduced. Several biocompatible materials can be employed in the practice of the present invention for the formation of a polymeric shell. For example, naturally occurring biocompatible materials such as, for example, proteins, polypeptides, oligopeptides, polynucleotides, polysaccharides (e.g., starch, cellulose, dextrans, alginates, chitosan, pectin, hyaluronic acid, and the like), and lipids are candidates for such modification.

As examples of suitable biocompatible materials, naturally occurring or synthetic proteins can be employed. Examples of suitable proteins include, for example, albumin, insulin, hemoglobin, lysozyme, immunoglobulins, α-2-macroglobulin, fibronectin, vitronectin, fibrinogen, casein, and the like, as well as combinations of any two or more thereof. Similarly, synthetic polymers can also be used for preparation of the drug formulation. Examples of suitable synthetic polymers include, for example, polyalkylene glycols (e.g., linear or branched chain), polyvinyl alcohol, polyacrylates, polyhydroxyethyl methacrylate, polyacrylic acid, polyethyloxazoline, polyacrylamides, polyisopropyl acrylamides, polyvinyl pyrrolidinone, polylactide/glycolide, and the like, and combinations thereof.

These biocompatible materials can also be employed in several physical forms, such as crosslinked or uncrosslinked gels, to provide matrices from which the propofol derivative can be released by diffusion and/or degradation of the matrix. Temperature sensitive materials can also be utilized as the dispersing matrix for the inventive compositions. Thus, for example, a propofol derivative can be injected in a liquid formulation of the temperature sensitive material (e.g., copolymers of polyacrylamides or copolymers of polyalkylene glycols and polylactide/glycolides) which gels at a specific site and provides slow release of the inventive compound.

Particles of biologic substantially completely contained within a polymeric shell, or associated therewith, prepared as described herein, are delivered neat, or optionally as a suspension in a biocompatible medium. This medium can be selected from water, buffered aqueous media, saline, buffered saline, optionally buffered solutions of amino acids, optionally buffered solutions of proteins, optionally buffered solutions of sugars, optionally buffered solutions of carbohydrates, optionally buffered solutions of vitamins, optionally buffered solutions of synthetic polymers, lipid-containing emulsions, and the like.

In addition, the polymeric shell can optionally be modified by a suitable agent, wherein the agent is associated with the polymeric shell through an optional covalent bond. Covalent bonds contemplated for such linkages include, for example, ester, ether, urethane, diester, amide, secondary or tertiary amine, phosphate ester, sulfate ester bonds, and the like. Suitable agents for the optional modification of the polymeric shell include, for example, synthetic polymers such as polyalkylene glycols (e.g., linear or branched chain polyethylene glycol), polyvinyl alcohol, polyhydroxyethyl methacrylate, polyacrylic acid, polyethyloxazoline, polyacrylamide, polyvinyl pyrrolidinone, and the like, phospholipids (e.g., phosphatidyl choline (PC), phosphatidyl ethanolamine (PE), phosphatidyl inositol (PI), sphingomyelin, and the like), proteins (e.g., enzymes, antibodies, and the like), polysaccharides (e.g., starch, cellulose, dextrans, alginates, chitosan, pectin, hyaluronic acid, and the like), chemical modifying agents (e.g., pyridoxal 5'-phosphate, derivatives of pyridoxal, dialdehydes, diaspirin esters, and the like), or combinations of any two or more thereof.

In one embodiment of the invention, nanoparticles of the inventive compounds can be administered by any acceptable route including, but not limited to, orally, intramuscularly, transdermally, intravenously, through an inhaler or other air borne delivery systems, and the like. When preparing the composition for injection, particularly for intravenous delivery, the continuous phase preferably comprises an aqueous solution of tonicity modifiers, buffered to a pH below 7, more preferably below 6.

The nanoparticles of this invention can be enclosed in a hard or soft capsule, can be compressed into tablets, or can be incorporated with beverages, food, or otherwise incorporated into the diet. Capsules can be formulated by mixing the nanoparticle with an inert pharmaceutical diluent and inserting the mixture into a hard gelatin capsule of the appropriate size. If soft capsules are desired, a slurry of the compound with an acceptable vegetable oil, light petroleum, or other inert oil can be encapsulated by machine into a gelatin capsule.

Compositions for inhalation or insufflation include solutions and suspensions in pharmaceutically acceptable aqueous or organic solvents, or mixtures thereof, and powders. The liquid compositions can contain suitable pharmaceutically acceptable excipients as set out above. Preferably the compositions are administered by the oral or nasal respiratory route for local or systemic effect. Compositions in sterile pharmaceutically acceptable solvents can be nebulised by use of inert gases. Nebulised solutions can be breathed directly from the nebulising device, or the nebulising device can be attached to a face mask, tent or intermittent positive pressure breathing machine. Solution, suspension, nanoparticle, or powder compositions can be administered, preferably orally or nasally, from devices which deliver the formulation in an appropriate manner.

The inventive pharmaceutical compositions can be therapeutically used for many suitable treatment regimens. In this respect, the inventive pharmaceutical compositions can be used for general anesthesia to facilitate surgery, drug or alcohol withdrawal, treatment of tetanus, and other diagnostic or therapeutic interventions. In particular, the inventive pharmaceutical composition can be used to maintain general anesthesia for extended periods (e.g., 24-48 hours) in addicted patients during which drug and/or alcohol withdrawal is provoked. The inventive pharmaceutical composition can be used to maintain general anesthesia for prolonged periods (e.g., days to weeks) in the management of patients with tetanus. The inventive pharmaceutical composition can be used as an oral sedative (e.g., sleeping pill). The inventive pharmaceutical composition also can be used to render patients sedated and pain-free to facilitate surgical and other therapeutic interventions (e.g., endotracheal mechanical ventilation and wound dressing change in patients with burns) or diagnostic procedures (e.g., endoscopy and imaging techniques) for which loss of consciousness is not required (i.e., "conscious sedation").

The inventive pharmaceutical compositions also are useful for treatment of migraine headaches. Migraine is a disorder characterized by a persistent headache that may be associated with visual disturbances, nausea, and vomiting. Although the precise cause of a migraine is unknown, it is hypothesized that migraines result from release of neurotransmitters by trigeminal nerves. The trigeminal nerves innervate cerebral blood vessels and inflammation occurs upon neurotransmitter release. Although the mechanism of action of alkyl phenols is not fully understood, propofol is known to be an agonist of $GABA_A$ receptors. Propofol's agonist activity leads to inhibition of neuronal firing which in turn contributes to its anesthetic properties.

The inventive pharmaceutical composition can be used as an antioxidant. It has been observed that alkylphenols, such as propofol, are very effective antioxidants (see, e.g., Peng et al., *Chin. Med. J. (Engl)*, 116(5), 731 (2003), and Tsuchiya et al., *Am. J. Respir. Crit. Care. Med.*, 165(1), 54 (2002)). Free radicals produced during oxidative stress can react with proteins, nucleic acids, lipids, and other biological macromolecules, producing damage to cells and tissues. Once formed, free radicals can interact to produce other free radicals and non-radical oxidants such as singlet oxygen and peroxides. A pharmaceutically effective amount of the inventive pharmaceutical composition can be used in treatment regimens for inhibition of oxidation in subjects that are at risk for developing a disease related to oxidative stress, such as cancer. Further, many neurodegenerative diseases such as Alzheimer's disease, Huntington's disease, Parkinson's disease, multiple sclerosis, and others are associated with oxidative stress. Other diseases that are associated with free radicals include ischemic reperfusion injury, inflammatory diseases, stroke, traumatic hemorrhage, spinal cord trauma, cataract formation, gastric ulcers, oxygen toxicity, undesired cell apoptosis, and radiation sickness.

The following examples further illustrate the invention but, should not be construed as in any way limiting its scope.

EXAMPLE 1

This example illustrates the preparation of (4-fluorophenyl)-(4-hydroxy-3,5-diisopropyl phenyl)methanone (CT7). To a solution of 2,6-diisopropylphenol (3.3 g, 18.5 mmol) in 98 mL of toluene were added dropwise 4-fluorobenzoyl chloride (4 mL, 37 mmol) and aluminum chloride (4.9 g, 37 mmol), while the temperature was maintained at room temperature. Stirring was continued for 7 hours and then the solvent was poured into ice-water. The mixture was extracted with ethyl acetate and hexane (1:9). The combined organic layers were washed with water and brine, dried ($Na_2SO_4$) and concentrated. The residue was purified by flash silica gel chromatography to generate the desired product as a yellowish solid. Yield 40%. $^1$H NMR (500 MHz, $CDCl_3$) δ 1.28 (d, J=6.8 Hz, 12H), 3.18 (hept, J=6.8 Hz, 2H), 5.34 (br s. 1H), 7.55 (s, 2H), 7.16 (d, d, J=8.6 Hz, 1H), 7.15 (d, J=8.6 Hz, 1H), 7.79 (d, J=8.6 Hz, 1H), 7.81 (d, J=8.6 Hz, 1H); Anal. Calcd for $(C_{19}H_{21}FO_2+H)^+$ and $(C_{19}H_{21}FO_2+H)^+$: 301 and 323. Found: 301 and 323.

EXAMPLE 2

This example illustrates the preparation of (4-(trifluoromethyl)phenyl)-(4-hydroxy-3,5-diisopropylphenyl)methanone (CT8). The title compound was prepared essentially as described in Example 1. $^1$H NMR (500 MHz, $CDCl_3$) δ 1.27 (d, J=6.6 Hz, 12H), 3.18 (hept, J=6.6 Hz, 2H), 5.40 (br s. 1H), 7.58 (s, 2H), 7.74 (d, J=8.0 Hz, 2H), 7.85 (d, J=8.0 Hz, 2H); Anal. Calcd for $(C_{20}H_{21}F_3O_2+H)^+$ and $(C_{20}H_{21}F_3O_2+Na)^+$: 351 and 373. Found: 351 and 373.

EXAMPLE 3

This example illustrates the preparation of (4-hydroxy-3,5-diisopropylphenyl)-(4-nitrophenyl)methanone (CY61). The title compound was prepared essentially as described in Example 1. $^1$H NMR (500 MHz, $CDCl_3$) δ 1.27 (d, J=6.9 Hz, 12H), 3.20 (hept, J=6.9 Hz, 2H), 5.73 (br s. 1H), 7.57 (s, 2H), 7.89 (d, J=8.8 Hz, 2H), 8.33 (d, J=8.8 Hz, 2H); Anal. Calcd for $(C_{19}H_{21}NO_4+H)^+$ and $(C_{19}H_{21}NO_4+Na)^+$: 328 and 350. Found: 328 and 350.

EXAMPLE 4

This example illustrates the preparation of (3-fluoro-4-(trifluoromethyl)phenyl)-(4-hydroxy-3,5-diisopropylphenyl)methanone (CY93) The title compound was prepared essentially as described in Example 1. $^1$NMR (500 MHz, $CDCl_3$) δ 1.28 (d, J=6.9 Hz, 12H), 3.18 (hept, J=6.9 Hz, 2H), 5.39 (s, 1H), 7.56 (s, 2H), 7.59-7.57 (m, 1H), 7.73 (t, J=8.1 Hz, 1H); Anal. Calcd for $C_{20}H_{21}F_4O_2$ (M+H) 369, found 369.

EXAMPLE 5

This example illustrates the preparation of (3-(trifluoromethyl)phenyl)-(4-hydroxy-3,5-diisopropylphenyl)methanone (CY96). The title compound was prepared essentially as described in Example 1. $^1$H NMR (500 MHz, $CDCl_3$) δ 1.27 (d, J=6.9 Hz, 12H), 3.21 (hept, J=6.6 Hz, 2H), 5.62 (br s. 1H), 7.58 (s, 2H), 7.63 (t, J=7.9 Hz, 1H), 7.83 (d, J=7.9 Hz, 1H), 7.98 (d, J=7.9 Hz, 1H), 8.02 (s, 1H); Anal. Calcd for $(C_{20}H_{21}F_3O_2+H)^+$ and $(C_{20}H_{21}F_3O_2+Na)^+$: 351 and 373. Found: 351 and 373.

EXAMPLE 6

This example illustrates the preparation of (3-fluoro-5-(trifluoromethyl)phenyl)-(4-hydroxy-3,5-diisopropylphenyl)methanone (CY97).

The title compound was prepared essentially as described in Example 1. $^1$H NMR (500 MHz, $CDCl_3$) δ 1.27 (d, J=6.9 Hz, 12H), 3.19 (hept, J=6.9 Hz, 2H), 5.41 (s, 1H), 7.53 (d, J=8.2 Hz, 1H), 7.56 (s, 2H), 7.68 (d, J=8.2 Hz, 1H), 7.80 (s, 1H). Anal. Calcd for $C_{20}H_{21}F_4O_2$ (M+H)$^+$ 369, found 369.

EXAMPLE 7

This example illustrates the preparation of (4-hydroxy-3,5-diisopropylphenyl)-(naphthalen-2-yl)methanone (CY99). The title compound was prepared essentially as described in Example 1. $^1$H NMR (500 MHz, $CDCl_3$) δ 1.28 (d, J=6.9 Hz, 12H), 3.20 (hept, J=6.9 Hz, 2H), 5.34 (s, 1H), 7.61-7.55 (m, 2H), 7.66 (s, 2H), 8.04-7.75 (m, 4H), 8.26 (s, 1H). Anal. Calcd for $C_{23}H_{25}O_2$ $(M+H)^+$ 333, found 333.

EXAMPLE 8

This example illustrates the preparation of (3,5-bis(trifluoromethyl)phenyl)-(4-hydroxy-3,5-diisopropylphenyl)methanone (CY104).

The title compound was prepared essentially as described in Example 1. $^1$H NMR (500 MHz, CDCl$_3$) δ 1.28 (d, J=6.9 Hz, 12H), 3.19 (hept, J=6.9 Hz, 2H), 5.41(br s. 1H), 7.56 (s, 2H), 8.07 (s, 1H), 8.22 (s, 2H); Anal. Calcd for $(C_{21}H_{20}F_6O_2+H)^+$ and $(C_{21}H_{20}F_6O_2+Na)^+$: 419 and 441. Found: 419 and 441.

EXAMPLE 9

This example illustrates the preparation of (4-tert-butylphenyl)-(4-hydroxy-3,5-diisopropylphenyl)methanone (CY120). The title compound was prepared essentially as described in Example 1. $^1$H NMR (500 MHz, CDCl$_3$) δ 1.28 (d, J=6.9 Hz, 12H), 1.37 (s, 9H), 3.18 (hept, J=6.9 Hz, 2H), 5.30 (br s. 1H), 7.49 (d, J=8.4 Hz, 2H), 7.60 (s, 2H), 7.73 (d, J=8.4 Hz, 2H); Anal. Calcd for $(C_{23}H_{30}O_2+H)^+$ and $(C_{23}H_{30}O_2+Na)^+$: 339 and 361. Found: 339 and 361.

EXAMPLE 10

This example illustrates the preparation of (4-hydroxy-3,5-diisopropylphenyl)-(4-isobutylphenyl)methanone (CY122). The title compound was prepared essentially as described in Example 1. $^1$H NMR (500 MHz, CDCl$_3$) δ 0.89 (t, J=7.4 Hz, 6H), 1.27 (d, J=5.5 Hz, 6H), 1.65 (m, 4H), 2.93 (tq, J=6.9, 6.9 Hz, 2H), 5.34 (br s. 1H), 7.52 (s, 2H), 7.74 (d, J=8.3 Hz, 2H), 7.84 (d, J=8.3 Hz, 2H); Anal. Calcd for $(C_{22}H_{25}F_3O_2+H)^+$ and $(C_{22}H_{25}F_3O_2+Na)^+$: 379 and 401. Found: 379 and 401.

EXAMPLE 11

This example illustrates the preparation of (4-hydroxy-3,5-diisopropylphenyl)-(4-iodophenyl)methanone (CY155). The title compound was prepared essentially as described in Example 1. $^1$H NMR (500 MHz, CDCl$_3$) δ 1.28 (d, J=6.9 Hz, 12H), 3.17 (hept, J=6.9 Hz, 2H), 5.31 (br s. 1H), 7.49 (d, J=8.3 Hz, 2H), 7.55 (s, 2H), 7.83 (d, J=8.3 Hz, 2H); Anal. Calcd for $(C_{19}H_{21}IO_2+H)^+$ and $(C_{19}H_{21}IO_2+Na)^+$: 409 and 433. Found: 409 and 433.

EXAMPLE 12

This example illustrates the preparation of (4-hydroxy-3,5-diisopropylphenyl)-(4-methoxyphenyl)methanone (CY157). The title compound was prepared essentially as described in Example 1. $^1$H NMR (500 MHz, CDCl$_3$) δ 1.20 (d, J=6.9 Hz, 12H), 2.97 (hept, J=6.9 Hz, 2H), 3.91 (s, 3H), 7.01 (d, J=8.8 Hz, 2H), 7.20 (s, 2H), 8.20 (dd, J=2.2, 6.8 Hz, 2H); Anal. Calcd for $(C_{20}H_{24}O_3+H)^+$: 313. Found: 313.

EXAMPLE 13

This example illustrates the preparation of (4-cyanophenyl)-(4-hydroxy-3,5-diisopropylphenyl)methanone (CY175). The title compound was prepared essentially as described in Example 1. $^1$H NMR (500 MHz, CDCl$_3$) δ 1.27 (d, J=6.8 Hz, 12H), 3.18 (hept, J=6.9 Hz, 2H), 5.40 (br s. 1H), 7.55 (s, 2H), 7.80 (ABq, Δγ=22.2 Hz, J=6.8 Hz, 2H), 7.81 (ABq, Δγ=22.2 Hz, J=6.6 Hz, 2H); Anal. Calcd for $(C_{20}H_{21}NO_2+H)^+$ and $(C_{20}H_{21}NO_2+Na)^+$: 308 and 330. Found: 308 and 330.

EXAMPLE 14

This example illustrates the preparation of (6-(trifluoromethyl)pyridin-3-yl)-(4-hydroxy-3,5-diisopropylphenyl)methanone (CY176).

The title compound was prepared essentially as described in Example 1. $^1$H NMR (500 MHz, CDCl$_3$) δ 1.29 (d, J=6.9 Hz, 12H), 3.18 (hept, J=6.9 Hz, 2H), 5.41 (br s. 1H), 7.59 (s, 2H), 7.84 (d, J=7.8 Hz, 1H), 8.24 (dd, J=8.1, 1.7 Hz, 1H), 9.03 (s, 1H); Anal. Calcd for $(C_{19}H_{20}F_3NO_2+H)^+$ and $(C_{19}H_{20}F_3NO_2+Na)^+$: 352 and 374. Found: 352 and 374.

EXAMPLE 15

This example illustrates the preparation of (4-bromophenyl)-(4-hydroxy-3,5-diisopropylphenyl)methanone (CY178). The title compound was prepared essentially as described in Example 1. $^1$H NMR (500 MHz, CDCl$_3$) δ 1.28 (d, J=6.9 Hz, 12H), 3.17 (hept, J=6.9 Hz, 2H), 5.33 (br s. 1H), 7.55 (s, 2H), 7.62 (m, 4H); Anal. Calcd for $(C_{19}H_{21}BrO_2+H)^+$ and $(C_{19}H_{21}BrO_2+Na)^+$: 362 and 364. Found: 363 and 383.

EXAMPLE 16

This example illustrates the preparation of (4-hydroxy-3,5-diisopropylphenyl)-(4-propylphenyl)methanone (CY181). The title compound was prepared essentially as described in Example 1. $^1$H NMR (500 MHz, CDCl$_3$) δ 0.98 (t, J=7.2, 3H), 1.28 (d, J=6.9 Hz, 12H), 1.69 (m, 2H), 2.67 (t, J=7.4, 2H), 3.18 (hept, J=6.9 Hz, 2H), 5.34 (br s. 1H), 7.27 (d, J=8.2 Hz, 2H), 7.59 (s, 2H), 7.71 (d, J=8.2 Hz, 2H); Anal. Calcd for $(C_{22}H_{28}O_2+H)^+$ and $(C_{22}H_{28}O_2+Na)+$: 325 and 347. Found: 325 and 327.

EXAMPLE 17

This example illustrates the preparation of (4-chlorophenyl)-(4-hydroxy-3,5-diisopropylphenyl)methanone (CY182). The title compound was prepared essentially as described in Example 1. H NMR (500 MHz, CDCl$_3$) δ 1.28 (d, J=6.9 Hz, 12H), 3.17 (hept, J=6.9 Hz, 2H), 5.31 (br s. 1H), 7.45 (d, J=8.5 Hz, 2H), 7.56 (s, 2H), 7.71 (d, J=8.5 Hz, 2H); Anal. Calcd for $(C_{19}H_{21}ClO_2+H)^+$ and $(C_{19}H_{21}ClO_2+Na)^+$: 317 and 339. Found: 317 and 319.

EXAMPLE 18

This example illustrates the preparation of 4-((4-(trifluoromethyl)phenyl)-(methoxyimino)methyl)-2,6-diisopropylphenol (CY127). To a solution of (4-(trifluoromethyl)phenyl)-(4-hydroxy-3,5-diisopropylphenyl)methanone (448 mg, 1.28 mmol), prepared in Example 2, in 8 mL of pyridine was added methoxyamine (1.07 g, 12.8 mmol) at room temperature. The reaction mixture was stirred at this temperature for 33 hrs and was concentrated. The residue was purified on silica gel flash column chromatography (hexanes:dichloromethane=3:2) to afford a yellow oil (485 mg, 99.9%). $^1$H NMR (500 MHz, CDCl$_3$) δ 1.27-1.21 (d, J=6.9 Hz, 12H), 3.20-3.00 (hept, J=6.9 Hz, 2H), 4.00+3.97 (s, 3H), 4.99+4.96 (s, 1H), 7.98-7.06 (m, 6H). Anal. Calcd for $C_{21}H_{23}F_3NO_2$ $(M-H)^-$ 378, found 378.

EXAMPLE 19

This example illustrates the preparation of 4-(4-(trifluoromethyl)benzyl)-2,6-diisopropylphenol (CY130). To a solution of (4-(trifluoromethyl)phenyl)-(4-hydroxy-3,5-diisopropylphenyl)methanone (486 mg, 1.4 mmol), prepared in Example 2, in 12 mL of dichloromethane at 0° C. was added trifluorosulfonic acid (0.6 mL, 5.5 mmol), followed by triethylsilane (0.7 mL, 4.1 mmol). The reaction mixture was stirred at this temperature for 36 hrs and quenched by saturated aqueous $NaHCO_3$ and extracted by ethyl ether (150 mL). The organic phase was washed by brine and dried over anhydrous $MgSO_4$. After filtration, the solution was concentrated in vacuo. The crude product was purified by silica gel flash column chromatography (toluene:hexanes=1:1) to afford the desired product as a white solid (100 mg, 21.4%). $^1$H NMR (500 MHz, $CDCl_3$) δ 1.23 (d, J=6.7 Hz, 6H), 1.24 (d, J=6.7 Hz, 6H), 3.13 (hept, J=6.9 Hz, 2H), 3.96 (s, 2H), 4.68 (s, 1H), 6.85 (s, 2H), 7.28 (d, J=8.1 Hz, 2H), 7.52 (d, J=8.1 Hz, 2H); Anal. Calcd for $C_{20}H_{22}F_3O_2$ (M−H) 351, found 351.

EXAMPLE 20

This example illustrates the preparation of 4-((4-(trifluoromethyl)phenyl)-(hydroxy)methyl)-2,6-diisopropylphenol (CY135). To a solution of (4-(trifluoromethyl)phenyl)-(4-hydroxy-3,5-diisopropylphenyl)methanone (308 mg, 0.9 mmol), prepared in Example 2, in reagent grade ethanol was added sodium borohydride (165 mg, 4.4 mmol) at room temperature. The reaction mixture was stirred for 11 hrs and quenched by 1N HCl and extracted by ethyl ether. The organic phase was washed by saturated aqueous NaHCO3 and brine, and was dried over anhydrous MgSO4. After filtration, the solution was condensed on rotavapor. The crude product was purified by silica gel flash column chromatography (hexanes:dichloromethane=1:2) to afford a white solid (100 mg, 33.8%). $^1$H NMR (500 MHz, $CDCl_3$) δ 1.25 (d, J=6.9 Hz, 12H), 3.13 (hept, J=6.9 Hz, 2H), 4.81 (s, 1H), 5.82 (s, 1H), 7.02 (s, 2H), 7.51 (d, J=8.1 Hz, 2H), 7.58 (d, J=8.1 Hz, 2H); Anal. Calcd for $C_{20}H_{22}F_3O$ (M−H)⁻ 335, found 335.

EXAMPLE 21

This example illustrates the preparation of 4-hydroxy-3,5-diisopropylphenyl)-(4-(methylsulfonyl)phenyl)methanone (CY177). To a solution of 4-methylsulfonylbenzoic acid (4.08 g, 24 mmol) and oxalyl chloride (3.9 mL, 44 mmol) in DCM (70 mL) at 0° C. was added three drops of DMF. The reaction mixture was stirred at room temperature for 3 hours and concentrated on a rotavapor. The residue was dissolved in 20 mL of DCM and was added into a suspension of 2,6-diisopropylphenol (2.12 g, 11.9 mmol) and aluminum chloride (1.6 g, 12 mmol in 50 mL of DCM. After being stirred for 14 hour, the reaction mixture was poured into 100 mL of ice-water and extracted with diisopropyl ether (2×100 mL). The organic layer was washed accordingly with 1N HCl, saturated aqueous $NaHCO_3$, and brine, and was dried over anhydrous $MgSO_4$. After filtration, the solution was condensed on a rotary evaporator. The crude product was suspended in 100 mL of methanol and 30 mL of water. The resultant suspension was treated with an excess amount of solid NaOH for 16 hour at room temperature and acidified by 1N HCl to pH of 4. The reaction mixture was extracted with ethyl acetate (2×100 mL). After washing with saturated aqueous $NaHCO_3$ and brine, the organic layer was dried over anhydrous $Na_2SO_4$ and filtered. The solution was concentrated and the residue was purified by flash silica gel chromatography to afford the desired product as a yellow solid (550 mg, Yield 13%). $^1$H NMR (500 MHz, $CDCl_3$) δ 1.27 (s, 6H), 1.29 (s, 6H), 3.12 (s, 3H), 3.18 (hept, J=6.9 Hz, 2H), 5.40 (br s, 1H), 7.57 (s, 2H), 7.90 (dd, J=6.6, 1.7 Hz, 2H), 8.06 (dd, J=6.5, 1.7 Hz, 2H); Anal. Calcd for $(C_{19}H_{21}FO_2+H)^+$: 361. Found: 361.

EXAMPLE 22

This example illustrates the preparation of pharmaceutical compositions comprising an inventive propofol derivative and albumin. 30 mg of 2,6-diisopropyl-4-(4-fluorobenzoyl)-phenol (as prepared in Example 1) was dissolved in 3.0 mL methylene chloride/methanol (9/1). The solution was then added into 27.0 mL of human serum albumin solution (3% w/v). The mixture was homogenized for 5 minutes at low RPM (Vitris homogenizer, model Tempest I.Q.) in order to form a crude emulsion, and then transferred into a high pressure homogenizer (Avestin). The emulsification was performed at 9000-40,000 psi while recycling the emulsion for at least 5 cycles. The resulting system was transferred into a Rotavap, and solvent was rapidly removed at 40° C. at reduced pressure (30 mm Hg), for 20-30 minutes. The resulting dispersion was translucent and the typical average diameter of the resulting particles was in the range 50-220 nm (Z-average, Malvern Zetasizer). The dispersion was further lyophilized for 48 hours. The resulting cake was easily reconstituted to the original dispersion by addition of sterile water or saline. The particle size after reconstitution was the same as before lyophilization. It should be recognized that the amounts, types, and proportions of drug, solvents, proteins used in this example are not limiting in anyway.

EXAMPLE 23

This example illustrates the formation of nanoparticles of inventive compounds by using cavitation and high shear forces during a sonication process. 20 mg of 2,6-diisopropyl-4-(4-fluorobenzoyl)-phenol (as prepared in Example 1) was dissolved in 1.0 mL methylene chloride. The solution was added to 4.0 mL of human serum albumin solution (5% w/v). The mixture was homogenized for 5 minutes at low RPM (Vitris homogenizer, model Tempest I.Q.) in order to form a crude emulsion, and then transferred into a 40 kHz sonicator cell. The sonication was performed at 60-90% power at 0° C. for 1 minute (550 Sonic Dismembrator). The mixture was transferred into a rotary evaporator, and methylene chloride was rapidly removed at 40° C., at reduced pressure (30 mm Hg), for 20-30 minutes. The typical diameter of the resulting particles was 300-420 nm (Z-average, Malvern Zetasizer).

The dispersion was further lyophilized for 48 hrs without adding any cryoprotectant. The resulting cake was easily reconstituted to the original dispersion by addition of sterile water or saline. The particle size after reconstitution was the same as before lyophilization.

EXAMPLE 24

This example illustrates the preparation of an oil-in-water formulation of the inventive compounds. An aqueous phase is prepared from glycerol (1.00-3.00% by weight), disodium edetate dihydrate (0.001-0.01% by weight), and water for injections (80-95% by weight). This mixture is stirred and taken to a temperature of approximately 60° C. In parallel to the above, an oil phase is prepared from soybean oil (1.00-10.0% by weight), the inventive compound (1.0-5.0% by weight) and egg phosphatide (0.5-2.0% by weight) in a vessel. The mixture is stirred at a temperature of approximately 70 to 75° C. until all ingredients are dissolved. Finally, the oil phase and water phase in the mixing vessel are homogenized for 5 minutes at low RPM (Vitris homogenizer, model Tempest I.Q.) in order to form a crude emulsion, and then transferred into a high-pressure homogenizer (Avestin). The emulsification is performed at 9000-40,000 psi while recycling the emulsion until the mean globule size of approximately 250 nM is achieved.

EXAMPLE 25

The propofol binding site on $GABA_A$ was defined using a series of competitive binding assays. Frozen bovine hippocampus was thawed and homogenized in 40 volumes of ice-cold 0.32 M sucrose. The suspension was centrifuged at 1000×g for 10 minutes at 4° C. The pellet was washed twice in assay buffer and reacted with radioactive ligand in presence or absence of propofol at 10−4 M final concentration. The amount of radioactivity remained on the Whatman filter following filtration of the reaction mix and two washes with assay buffer was determined using a liquid scintillation counter. Inhibition of radioactive ligand binding by propofol represents the competitive binding of propofol to the same site as the radioactive ligand. $GABA_A$ agonist site, $GABA_A$ α-1 site, $GABA_A$ α-5 site, $GABA_A$ α-6 site, and $GABA_A$ Cl channel were assayed using $^3$H-GABA, $^3$H-Flunitrazepam, $^3$H-RY80, $^3$H-Ro 15-4513, and $^3$H-TBOB.

The data in Table 1 illustrates that propofol exhibited specific binding to the $GABA_A$ Cl channel. Binding to other sites was not observed.

TABLE 1

Specific binding of propofol to the $GABA_A$ chloride channel.

| GABA Domain | Percent Inhibition |
| --- | --- |
| agonist site | 12.48 |
| alpha 1 site | −14.31 |
| alpha 2 site | −15.58 |
| alpha 6 site | −0.89 |
| chloride channel | 117.52 |

Propofol at 10$^{-4}$ M only inhibited the binding of TBOB to the chloride channel of the $GABA_A$ receptor. No significant inhibition of the agonist site, the alpha 1 site, the alpha 2 site, or the alpha 6 site was observed.

EXAMPLE 26

To determine the binding constant ($K_D$) of propofol and its analogs for $GABA_A$ Cl channel, binding was determined as in Example 25 in presence of increasing concentration of propofol and the $K_D$ determined graphically using the Hill plots. The data are shown in Table 2. In vivo hypnotic activity was determined as follows. Drugs solubilized in DMSO were administered to rats by tail vein injection (N=5 rats per group). A dose level of 28 μmol/kg (5 mg/kg for propofol) was used to compensate for differences in molecular weight of the analogs. Anesthetic activity in vivo was determined as time to recovery of righting reflex following administration of the compounds. There was significant correlation between in vitro $GABA_A$ binding and in vivo anesthetic activity. Furthermore, it was found that propofol at 5 mg/kg (28 mmol/kg) anesthetized rats for 20 min; while, propofol analogs CT8 and CY155 at equivalent dose anesthetized the rats for 75-92 min and 86 min, respectively.

TABLE 2

Activity of propofol and propofol analogs in vitro and in vivo.

| Chemical Structure | $GABA_A$ Cl Channel Binding (IC$_{50}$, μM) | Anesthesia Activity (Time to awakening, min) |
| --- | --- | --- |
| Propofol | 4.86 | 20.6 + 9.0, N = 4 |
| CT7 | | 34.2 + 1.2, N = 2 |
| CT8 | 0.57 | 92.5 + 5.0, N = 4 |
| CY61 | 0.5 | 57.2 + 0.7, N = 5 |
| CY62 | 31.6 | 0 + 0, N = 5 |
| CY93 | 1.27 | 52.4 + 37.7, N = 3 |
| CY96 | 3.91 | 5.5 + 2.4, N = 5 |
| CY97 | 4.67 | 1.9 + 1.0, N = 5 |
| CY99 | No activity | 5.5 + 3.4, N = 5 |
| CY104 | 21.3 | 6.4 + 2.8, N = 4 |
| CY120 | | 15.5 + 9.2, N = 2 |
| CY122 | | 7.6 + 1.8, N = 5 |
| CY127 | | 8.8 + 5.8, N = 5 |
| CY130 | | 8.2 + 3.0, N = 5 |
| CY135 | | 15.0 + 11.4, N = 5 |
| CY155 | 0.57 | 86.1 + 22.1, N = 5 |
| CY157 | | 0.0 + 0.0, N = 5 |
| CY175 | | 43.4 + 23.5, N = 2 |
| CY176 | | 14.9 + 21.1, N = 2 |
| CY177 | | 4.6 + 1.5, N = 5 |
| CY178 | | 66.6 + 17.9, N = 5 |
| CY181 | | 9.0 + 20.1, N = 5 |
| CY182 | | 67.7 + 5.1, N = 3 |

EXAMPLE 27

To explore the potential clinical application of CT8, its therapeutic index was compared to that of propofol. Dose escalation experiment was performed in rat in order to compare the toxicity and the pharmacodynamic of CT8 against propofol. Drugs solubilized in DMSO were administered to rats (5 rats per group). Anesthetic activity in vivo was determined as time to recovery of righting reflex. Mortality was also monitored and the LD50 curves for propofol and CT8 constructed. In order to adjust for the differences in molecular weight between the two compounds, μmol/kg dose was used. As shown in Table 3, CT8 exhibited the same toxicity profile as propofol with a calculated LD10 of 29 μmol/kg in comparison to the calculated LD10 of 28 μmol/kg for propofol. The LD50 of propofol and CT8 were calculated to be 45.3 μmol/kg and 62.1 μmol/kg, respectively. And as shown in Table 4, there was a linear dose response for anesthetic activity for both CT8 and propofol. However, CT8 exhibited higher anesthetic activity in vivo than propofol. At LD10, the rats were asleep for 1.73 hr when treated with CT8 and only 0.35 hr when treated with propofol.

TABLE 3

Mortality curves.

| | Mortality (%) | |
| --- | --- | --- |
| Dose (μmol/kg) | CT8 | Propofol |
| 112.1894 | — | 100 |
| 56.09469 | — | 80 |
| 28.04734 | — | 10 |
| 5.609469 | — | 0 |
| 114.2368 | 100 | — |
| 228.4735 | 100 | — |
| 57.11838 | 40 | — |
| 28.55919 | 10 | — |
| 14.2796 | 0 | — |
| 2.855919 | 0 | — |
| 1.427959 | 0 | — |

TABLE 4

Anesthesia response curves.

| Dose (μmol/kg) | Time to Awakening (h) [mean ± SD, (N)] | |
|---|---|---|
| | CT8 | Propofol |
| 56.09 | — | 0.600 ± 0.000, (1) |
| 28.05 | — | 0.346 ± 0.149, (4) |
| 28.05 | — | 0.350 ± 0.228 (5) |
| 5.61 | — | 0.000 ± 0.000, (5) |
| 57.12 | 3.553 ± 0.166, (3) | — |
| 28.56 | 1.728 ± 0.154 (5) | — |
| 28.10 | 1.543 ± 0.085, (4) | — |
| 14.28 | 0.748 ± 0.094, (5) | — |
| 2.86 | 0.000 ± 0.000, (5) | — |
| 1.43 | 0.000 ± 0.000, (5) | — |

EXAMPLE 28

To further explore the potential clinical application of CT8, its PK in rat was compared to that of propofol. This study used male Sprague-Dawley rat. The rats were assigned to three groups (N=3 per group) to receive single i.v. bolus propofol at 5 mg/kg and or CT8 at 10 mg/kg. The drugs were dissolved in DMSO to 12.5 mg/mL and 25 mg/mL for propofol and CT8, respectively; and administered at 0.4 mL/kg iv. Blood was drawn at 1, 3, 5, 10, 30, 60, 120, and 240 minutes after dosing.

EDTA anticoagulated blood was analyzed for propofol using GC/MS, with thymol as internal standard. The analysis was performed on a J & W 30 m×0.32 mm DB-5 capillary column with a 0.25 um film of phenylmethyl silicone. The gas chromatograph, a Hewlett-Packard Model 6890N was equipped with a 5973 mass selective detector operating in the electron impact mode (70 eV) with selected ion monitoring. The detector monitored the 163.1 m/z fragment for propofol/CT8 and 135.1 n/z fragment for thymol. The data was processed with HP1034C mass spectrometer control software. The standard curve showed good linearity with r2=0.98. Pharmacokinetic parameters were calculated using WinNonlin 4.0.1 program.

As shown in Table 5, CT8 has a smaller volume of distribution than that of propofol, especially in V1—the distribution phase, suggesting that it is having difficulty penetrating peripheral tissues. CT8 V1, V2, and Vss were 375×, 11×, and 14× smaller than those of propofol. Consequently, AUC was higher for CT8 than that of propofol (317× higher) and CL was slower for CTS than propofol (146× slower). These PK properties disqualified CT8 as an anesthetic agent; however, it is making CT8 a very attractive sleeping pill agent such as Ambien.

TABLE 5

PK parameters of CT8 and propofol in rat.

| | AUC (hr*ug/mL) | Cmax (ug/mL) | V1 (L/kg) | CL (L/hr/kg) | Vss (L/kg) | V2 (L/kg) |
|---|---|---|---|---|---|---|
| CT8 | 127 | 283 | 0.04 | 0.08 | 5.3 | 5.2 |
| Propofol | 0.4 | 0.3 | 15.0 | 11.7 | 73.0 | 58.0 |

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound of the formula

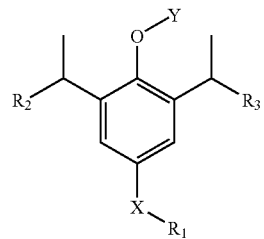

wherein
X is C=O and Y=H, $R_1$ is $C_4$-$C_{20}$ aryl, $R_2$ is hydrogen, and $R_3$ is methyl, ethyl or propyl with the proviso that $R_1$ is not phenyl.

2. A compound of the formula

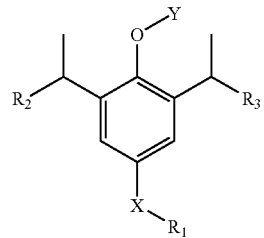

wherein
$R_1$ is selected from the group consisting of 4-fluorophenyl, 3-fluorophenyl, 2-fluorophenyl, 4-bromophenyl, 3-bromophenyl, 2-bromophenyl, 4-chlorophenyl, 3-chlorophenyl, 2-chlorophenyl, 4-trifluoromethylphenyl, 3-trifluoromethylphenyl, 2-trifluoromethylphenyl, 4-methoxyphenyl, 3-methoxyphenyl, 2-methoxyphenyl, 4-nitrophenyl, 3-nitrophenyl, 2-nitrophenyl, 4-cyanophenyl, 3-cyanophenyl, 2-cyanophenyl, 2-methylphenyl, 4-methylphenyl, 3-chloromethylphenyl, 2-iodophenyl, 4-iodophenyl, 4-trifluoromethoxyphenyl, 3-propylphenyl, 2-ethylphenyl, 4-bromomethylphenyl, 4-dimethylaminophenyl, 4-biphenyl, 1-naphthalenyl, 2-naphthalenyl, 2-furanyl, 5-nitro-2-furanyl, 2-thiophenyl, 3,4-methylenedioxyphenyl, 2,3-difluorophenyl, 2,4-difluorophenyl, 2,5-difluorophenyl, 2,6-difluorophenyl, 3,4-difluorophenyl, 3,5-difluorophenyl, 2,4-dichlorophenyl, 2,6-dichlorophenyl, 3,5-dichlorophenyl, 2,5-bis(trifluoromethyl)phenyl, 3,5-bis(trifluoromethyl)phenyl, 4-chloro-3-nitrophenyl, 5-bromo-2- methoxyphenyl, 4-methyl-3-nitrophenyl, 2-fluoro-3-trifluoromethylphenyl, 2-fluoro-5-trifluoromethylphenyl, 2-fluoro-6-trifluoromethylphenyl, 3-fluoro-4-trifluoromethylphenyl, 3-fluoro-5-trifluoromethylphenyl, 2,4-dimethoxyphenyl, 2,6-dimethoxyphenyl, 3,4-dimethoxyphenyl, 3,5-dimethoxyphenyl, 3,5-dichloro-4-methoxyphenyl, 2,3,4-trifluorophenyl, 2,3,6-trifluorophenyl, 2,4,5-trifluorophenyl, 2,4,6-trichlorophenyl, 2,4-dichloro-5-fluorophenyl, 3,4,5-trimethoxyphenyl, 2,4,5-trifluoro-3-methoxyphenyl, 2,3,4,5-tetrafluorophenyl, and pentafluorophenyl;

$R_2$ and $R_3$ are $C_1$-$C_6$ alkyl;

X is C=O, C=S, C=C, $CR_4R_5$, $C(OR_6)R_7$ or C=N—$OR_8$;

Y is hydrogen, $COR_4$, $COOR_4$, $CONR_4R_5$, $COSR_4$ or phosphate;

wherein $R_4$, $R_5$, $R_6$, $R_7$ and $R_8$ are hydrogen or $C_1$-$C_6$ alkyl.

3. The compound of claim 2, wherein Y is H.

4. A compound of the formula

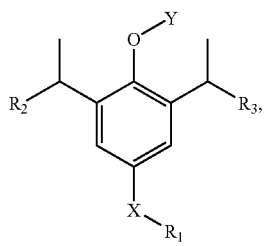

wherein Y is phosphate;

$R_1$ is hydrogen, $C_1$-$C_6$ alkyl, or $C_4$-$C_{20}$ aryl;

$R_2$ and $R_3$ are $C_1$-$C_6$ alkyl;

X is C=O, C=S, C=C, $CR_4R_5$, $C(OR_6)R_7$ or C=N—$OR_8$;

wherein $R_4$, $R_5$, $R_6$, $R_7$ and $R_8$ are hydrogen or $C_1$-$C_6$ alkyl;

except when X is C=O and $R_2$ and $R_3$ are methyl, then $R_1$ is not phenyl.

5. A compound of the formula

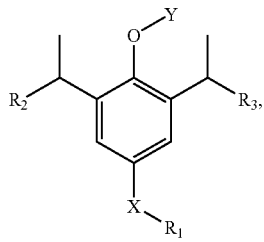

wherein X is C=O, $R_1$ is 4-chlorophenyl, and $R_2$ and $R_3$ are each methyl;

Y is hydrogen, $COR_4$, $COOR_4$, $CONR_4R_5$, $COSR_4$ or phosphate; and $R_4$, $R_5$, $R_6$, $R_7$ and $R_8$ are hydrogen or $C_1$-$C_6$ alkyl.

6. A compound of the formula

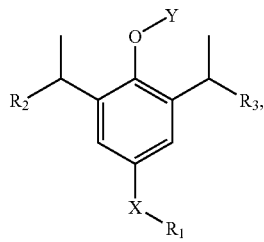

wherein X is C=O and Y is H, $R_1$ is 4-chlorophenyl, and $R_2$ and $R_3$ are each methyl; and $R_4$, $R_5$, $R_6$, $R_7$ and $R_8$ are hydrogen or $C_1$-$C_6$ alkyl.

7. A compound of the formula

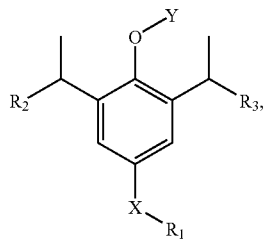

wherein X is C=O, $R_1$ is 4-trifluoromethylphenyl, and $R_2$ and $R_3$ are each methyl;

Y is hydrogen, $COR_4$, $COOR_4$, $CONR_4R_5$, $COSR_4$ or phosphate; and $R_4$, $R_5$, $R_6$, $R_7$ and $R_8$ are hydrogen or $C_1$-$C_6$ alkyl.

8. A compound of the formula

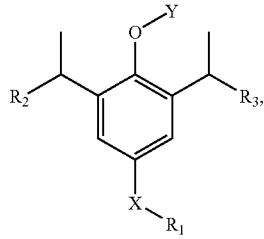

wherein X is C=O and Y is H, $R_1$ is 4-trifluoromethylphenyl, and $R_2$ and $R_3$ are each methyl; and $R_4$, $R_5$, $R_6$, $R_7$ and $R_8$ are hydrogen or $C_1$-$C_6$ alkyl.

9. A compound of the formula

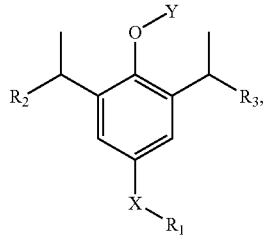

wherein X is C=O, $R_1$ is 4-iodophenyl, and $R_2$ and $R_3$ are each methyl;

Y is hydrogen, $COR_4$, $COOR_4$, $CONR_4R_5$, $COSR_4$ or phosphate; and $R_4$, $R_5$, $R_6$, $R_7$ and $R_8$ are hydrogen or $C_1$-$C_6$ alkyl.

10. A compound of the formula

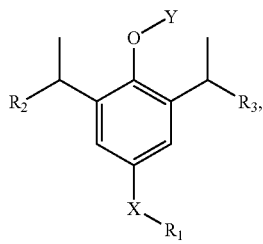

wherein X is C=O and Y is H, $R_1$ is 4-iodophenyl, and $R_2$ and $R_3$ are each methyl; and $R_4$, $R_5$, $R_6$, $R_7$ and $R_8$ are hydrogen or $_{1-6}$ alkyl.

11. A pharmaceutical composition comprising a therapeutically effective amount of the compound of claim 2 and a pharmaceutically acceptable carrier.

12. A pharmaceutical composition comprising a therapeutically effective amount of the compound of claim 3 and a pharmaceutically acceptable carrier.

13. A pharmaceutical composition comprising a therapeutically effective amount of the compound of claim 4 and a pharmaceutically acceptable carrier.

14. A pharmaceutical composition comprising a therapeutically effective amount of the compound of claim 5 and a pharmaceutically acceptable carrier.

15. A pharmaceutical composition comprising a therapeutically effective amount of the compound of claim 6 and a pharmaceutically acceptable carrier.

16. A pharmaceutical composition comprising a therapeutically effective amount of the compound of claim 7 and a pharmaceutically acceptable carrier.

17. A pharmaceutical composition comprising a therapeutically effective amount of the compound of claim 8 and a pharmaceutically acceptable carrier.

18. A pharmaceutical composition comprising a therapeutically effective amount of the compound of claim 9 and a pharmaceutically acceptable carrier.

19. A pharmaceutical composition comprising a therapeutically effective amount of the compound of claim 10 and a pharmaceutically acceptable carrier.

20. A method of inducing sedation, hypnosis and/or sleep effect, or general anesthesia in a patient, which method comprises administering to the patient a therapeutically effective amount of the compound of claim 2.

21. A method of inducing sedation, hypnosis and/or sleep effect, or general anesthesia in a patient, which method comprises administering to the patient a therapeutically effective amount of the compound of claim 3.

22. A method of inducing sedation, hypnosis and/or sleep effect, or general anesthesia in a patient, which method comprises administering to the patient a therapeutically effective amount of the compound of claim 4.

23. A method of inducing sedation, hypnosis and/or sleep effect, or general anesthesia in a patient, which method comprises administering to the patient a therapeutically effective amount of the compound of claim 5.

24. A method of inducing sedation, hypnosis and/or sleep effect, or general anesthesia in a patient, which method comprises administering to the patient a therapeutically effective amount of the compound of claim 6.

25. A method of inducing sedation, hypnosis and/or sleep effect, or general anesthesia in a patient, which method comprises administering to the patient a therapeutically effective amount of the compound of claim 7.

26. A method of inducing sedation, hypnosis and/or sleep effect, or general anesthesia in a patient, which method comprises administering to the patient a therapeutically effective amount of the compound of claim 8.

27. A method of inducing sedation, hypnosis and/or sleep effect, or general anesthesia in a patient, which method comprises administering to the patient a therapeutically effective amount of the compound of claim 9.

28. A method of inducing sedation, hypnosis and/or sleep effect, or general anesthesia in a patient, which method comprises administering to the patient a therapeutically effective amount of the compound of claim 10.

* * * * *